(12) United States Patent
Keil et al.

(10) Patent No.: US 8,207,146 B2
(45) Date of Patent: Jun. 26, 2012

(54) PHENOTHIAZINE DERIVATIVE HAVING A DOUBLE BOND, METHOD FOR THE PRODUCTION THEREOF, AND USE THEREOF AS A PHARMACEUTICAL

(75) Inventors: Stefanie Keil, Hofheim (DE); Elisabeth Defossa, Idstein (DE); Dieter Schmoll, Frankfurt (DE); Axel Dietrich, Frankfurt (DE); Johanna Kuhlmann-Gottke, Frankfurt (DE); Karl-Christian Engel, Frankfurt (DE)

(73) Assignee: Sanofi-Aventis, Paris (FR)

( * ) Notice: Subject to any disclaimer, the term of this patent is extended or adjusted under 35 U.S.C. 154(b) by 128 days.

(21) Appl. No.: 12/724,520

(22) Filed: Mar. 16, 2010

(65) Prior Publication Data

US 2010/0261643 A1 Oct. 14, 2010

Related U.S. Application Data

(63) Continuation of application No. PCT/EP2008/007219, filed on Sep. 4, 2008.

(30) Foreign Application Priority Data

Sep. 21, 2007 (EP) .................................... 07291133

(51) Int. Cl.
*A61K 31/675* (2006.01)
*C07D 279/00* (2006.01)
(52) U.S. Cl. ............ 514/80; 514/225.2; 544/14; 544/31
(58) Field of Classification Search ........................ None
See application file for complete search history.

(56) References Cited

U.S. PATENT DOCUMENTS

| | | | | |
|---|---|---|---|---|
| 6,608,038 B2 * | 8/2003 | Caplan et al. | ............... | 514/44 R |
| 7,220,771 B2 * | 5/2007 | Bhagwat et al. | ............. | 514/403 |
| 2001/0041727 A1 * | 11/2001 | Marshall et al. | ............. | 514/367 |
| 2003/0153509 A1 * | 8/2003 | Bachovchin et al. | ........... | 514/19 |

FOREIGN PATENT DOCUMENTS

| | | |
|---|---|---|
| WO | WO 01/44216 | 6/2001 |
| WO | WO 0144216 A1 * | 6/2001 |
| WO | WO 02/062772 | 8/2002 |
| WO | WO 02062772 A1 * | 8/2002 |
| WO | WO 03059864 A2 * | 7/2003 |
| WO | WO 2005/095417 | 10/2005 |
| WO | WO 2005095417 A1 * | 10/2005 |

OTHER PUBLICATIONS

Lindenmayer, Jean-Pierre, Treatment of Refractory Schizophrenia, Psychiatric Quarterly, vol. 71, No. 4, Winter (2000).*
Azzouz, Mioun, Gene Therapy for ALS: Progress and Prospects, Biochemica et Biophysica Acta 1762 1122-1127 (2006).*
Citron, Martin Alzheimer's diasease: treatments in discovery and development, Nature Nueroscience Supplement, vol. 5, 1055-1057, Nov. 2002.*
Korczyn and Mussbaum, Emerging Therapies in the Pharmacological Treatment of Parkinson's Disease, Drugs, (62) 775-766, (2002).*
Margolis, Russell. Diagnosis of Huntington's Disease, Clinical Chemistry (49:10) 1726-1732 (2003).*
Martin, Lee. Nuerodegeneration in exitotoxicity, global cerebral ischemia, and target deprivation: A perspective on the contributions of aptopsis and necrosis, Brain Research Bulletin, vol. 46, No. 4, 281-309 (1998).*
Mattson, Mark P. Pathways Towards and Away from Alzheimer's Disease, Nature, vol. 430, 631-639, (2004).*
Patel, ShirishV. pharmacotherapy of Cognitive Impairment in Alzheimer's Disease: A Review. Journal of Geriatric Psychiatry and Neurology, vol. 8 81-95 (1995).*
Nicotine addiction; http://emedicine.medscape.com/article/287555-treatment last visited (Dec. 2, 2011).*
Drug dependence, a Chronic Medical Illness, JAMA, 284: 1719-1720 Oct. 4, 2000.*

* cited by examiner

*Primary Examiner* — Christina Bradley
*Assistant Examiner* — Jeanette Lieb
(74) *Attorney, Agent, or Firm* — Scully, Scott, Murphy & Presser, P.C.

(57) ABSTRACT

The present invention relates to substituted phenothiazines with a double bond and physiologically acceptable salts thereof, and their use as a medicament.

9 Claims, No Drawings

PHENOTHIAZINE DERIVATIVE HAVING A DOUBLE BOND, METHOD FOR THE PRODUCTION THEREOF, AND USE THEREOF AS A PHARMACEUTICAL

This application is a Continuation of International Application No. PCT/EP2008/007219, filed Sep. 4, 2008, which is incorporated herein by reference in its entirety.

The present invention relates to substituted phenothiazines with a double bond and physiologically acceptable salts thereof.

Phenothiazine derivatives such as, for example, chlorpromazine (3-(2-chloro-4a,10a-dihydro-10H-phenothiazin-10-yl)-N,N-dimethylpropane-1-amine) are already known as neuroleptics.

It was an object of the present invention to develop compounds for the treatment of diabetes. In particular, these compounds should lower the blood glucose level.

Accordingly, the invention relates to compounds of the formula I,

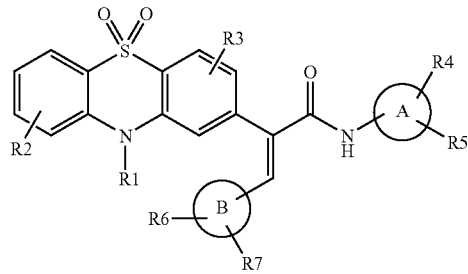

I in which
R1 is H, $(C_1-C_6)$-alkyl, $(C_0-C_6)$-alkylene-aryl, CO—$(C_1-C_6)$-alkyl, $(C_2-C_6)$-alkylene-COO—$(C_0-C_6)$-alkyl, $(C_2-C_6)$-alkylene-O—$(C_1-C_6)$-alkyl R2, R3 independently of one another are H, F, Cl, Br, CN, $NO_2$, $(C_0-C_6)$-alkylene-COO—$(C_0-C_6)$-alkyl, $(C_0-C_6)$-alkylene-O—$(C_0-C_6)$-alkyl, $(C_1-C_6)$-alkyl, $(C_0-C_6)$-alkylene-CO—$(C_1-C_6)$-alkyl, $(C_0-C_6)$-alkylene-phenyl, $SCF_3$, $SF_5$, $SCH_3$;

R4, R5 independently of one another are H, F, Cl, Br, CN, SCN, $NO_2$, $(C_0-C_6)$-alkylene-COO—$(C_0-C_6)$-alkyl, —CO—COO—$(C_0-C_6)$-alkyl, $(C_0-C_6)$-alkylene-O—$(C_0-C_6)$-alkyl, $(C_1-C_6)$-alkyl, $(C_0-C_6)$-alkylene-CO—$(C_1-C_6)$-alkyl, $(C_0-C_6)$-alkylene-CONH$(C_0-C_6)$-alkyl, $(C_0-C_6)$-alkylene-CON$[(C_0-C_6)$-alkyl$]_2$, $(C_0-C_6)$-alkylene-NH$(C_0-C_6)$-alkyl, $(C_0-C_6)$-alkylene-NH—COO—$(C_0-C_6)$-alkyl, $(C_0-C_6)$-alkylene-CON$[(C_0-C_6)$-alkyl$]$-O—$(C_0-C_6)$-alkyl, $(C_0-C_6)$-alkylene-N$[(C_0-C_6)$-alkyl$]_2$, $(C_0-C_6)$-alkylene-aryl, $SF_5$, $(C_0-C_6)$-alkyl-$S(O)_x(C_1-C_6)$-alkyl, $S(O)_x(C_1-C_6)$-alkylene-COO—$(C_0-C_6)$-alkyl, $S(O)_x(C_2-C_6)$-alkylene-O—$(C_0-C_6)$-alkyl, —$SO_2$—NH—$(C_0-C_6)$-alkyl, —$SO_2$—N—$[(C_0-C_6)$-alkyl$]_2$, $S(O)_x(C_0-C_6)$-alkylene-heterocycle, $S(O)_x(C_1-C_6)$-alkylene-CO-heterocycle, —NH—$SO_2$—$(C_1-C_6)$-alkyl, $(C_0-C_6)$-alkylene-cycloalkyl, $(C_0-C_6)$-alkylene-heterocycle, $(C_0-C_6)$-alkylene-aryl;

R6, R7 independently of one another are H, F, Cl, Br, CN, $NO_2$, =O, =S, =N—O—$(C_0-C_6)$-alkyl, $(C_0-C_6)$-alkylene-COO—$(C_0-C_6)$-alkyl, $(C_0-C_6)$-alkylene-O—$(C_0-C_6)$-alkyl, $(C_0-C_6)$-alkylene-O—CO—$(C_1-C_6)$-alkyl, $(C_1-C_6)$-alkyl, $(C_0-C_6)$-alkylene-CO—$(C_1-C_6)$-alkyl, $(C_0-C_6)$-alkylene-aryl, $SF_5$, $S(O)_x$—$(C_1-C_6)$-alkyl;

x 0, 1, 2;

A is a 5- to 10-membered heterocycle, where the heterocycle may be fused to a further 5- to 10-membered ring;

B is a 4- to 8-membered cycloalkyl ring, a 4- to 10-membered heterocycle or a 6- to 10-membered aryl ring;

and physiologically acceptable salts thereof.

Preference is given to compounds of the formula I in which one or more radicals have the following meaning:

R1 is H, $(C_1-C_6)$-alkyl, $(C_0-C_6)$-alkylene-aryl, CO—$(C_1-C_6)$-alkyl, $(C_2-C_6)$-alkylene-COO—$(C_0-C_6)$-alkyl, $(C_2-C_6)$-alkylene-O—$(C_1-C_6)$-alkyl R2, R3 independently of one another are H, F, Cl, Br, CN, $NO_2$, $(C_0-C_6)$-alkylene-COO—$(C_0-C_6)$-alkyl, $(C_0-C_6)$-alkylene-O—$(C_0-C_6)$-alkyl, $(C_1-C_6)$-alkyl, $(C_0-C_6)$-alkylene-CO—$(C_1-C_6)$-alkyl, $(C_0-C_6)$-alkylene-phenyl, $SCF_3$, $SF_5$, $SCH_3$;

R4, R5 independently of one another are H, F, Cl, Br, CN, SCN, $NO_2$, $(C_0-C_6)$-alkylene-COO—$(C_0-C_6)$-alkyl, —CO—COO—$(C_0-C_6)$-alkyl, $(C_0-C_6)$-alkylene-O—$(C_0-C_6)$-alkyl, $(C_1-C_6)$-alkyl, $(C_0-C_6)$-alkylene-CO—$(C_1-C_6)$-alkyl, $(C_0-C_6)$-alkylene-CONH$(C_0-C_6)$-alkyl, $(C_0-C_6)$-alkylene-CON$[(C_0-C_6)$-alkyl$]_2$, $(C_0-C_6)$-alkylene-NH$(C_0-C_6)$-alkyl, $(C_0-C_6)$-alkylene-NH—COO—$(C_0-C_6)$-alkyl, $(C_0-C_6)$-alkylene-CON$[(C_0-C_6)$-alkyl$]$-O—$(C_0-C_6)$-alkyl, $(C_0-C_6)$-alkylene-N$[(C_0-C_6)$-alkyl$]_2$, $(C_0-C_6)$-alkylene-aryl, $SF_5$, $(C_0-C_6)$-alkyl-$S(O)_x(C_1-C_6)$-alkyl, $S(O)_x(C_1-C_6)$-alkylene-COO—$(C_0-C_6)$-alkyl, $S(O)_x(C_2-C_6)$-alkylene-O—$(C_0-C_6)$-alkyl, —$SO_2$—NH—$(C_0-C_6)$-alkyl, —$SO_2$—N—$[(C_0-C_6)$-alkyl$]_2$, $S(O)_x(C_0-C_6)$-alkylene-heterocycle, $S(O)_x(C_1-C_6)$-alkylene-CO-heterocycle, —NH—$SO_2$—$(C_1-C_6)$-alkyl, $(C_0-C_6)$-alkylene-cycloalkyl, $(C_0-C_6)$-alkylene-heterocycle, $(C_0-C_6)$-alkylene-aryl;

R6, R7 independently of one another are H, F, Cl, Br, CN, $NO_2$, =O, =S, =N—O—$(C_0-C_6)$-alkyl, $(C_0-C_6)$-alkylene-COO—$(C_0-C_6)$-alkyl, $(C_0-C_6)$-alkylene-O—$(C_0-C_6)$-alkyl, $(C_0-C_6)$-alkylene-O—CO—$(C_1-C_6)$-alkyl, $(C_1-C_6)$-alkyl, $(C_0-C_6)$-alkylene-CO—$(C_1-C_6)$-alkyl, $(C_0-C_6)$-alkylene-aryl, $SF_5$, $S(O)_x$—$(C_1-C_6)$-alkyl;

x 0, 1, 2;

A is a 5- to 10-membered heterocycle, where the heterocycle may be fused to a further 5- to 10-membered ring;

B is a 4- to 8-membered cycloalkyl ring;

and physiologically acceptable salts thereof.

Particular preference is given to compounds of the formula I in which one or more radicals have the following meaning:

R1 is H, $(C_1-C_6)$-alkyl, $(C_0-C_6)$-alkylene-aryl, CO—$(C_1-C_6)$-alkyl, $(C_2-C_6)$-alkylene-COO—$(C_0-C_6)$-alkyl, $(C_2-C_6)$-alkylene-O—$(C_1-C_6)$-alkyl R2, R3 are H;

R4 is $(C_1-C_6)$-alkyl, O—$(C_1-C_6)$-alkyl, $(C_0-C_6)$-alkylene-aryl;

R5 is H;

R6, R7 independently of one another are H, F, Cl, Br, CN, $NO_2$, =O, =S, =N—O—$(C0-C_6)$-alkyl, $(C_0-C_6)$-alkylene-COO—$(C_0-C_6)$-alkyl, $(C_0-C_6)$-alkylene-O—$(C_0-C_6)$-alkyl, $(C_0-C_6)$-alkylene-O—CO—$(C_1-C_6)$-alkyl, $(C_1-C_6)$-alkyl, $(C_0-C_6)$-alkylene-CO—$(C_1-C_6)$-alkyl, $(C_0-C_6)$-alkylene-aryl, $SF_5$, $S(O)_x$—$(C_1-C_6)$-alkyl;

x 0, 1, 2;

A is a 5- to 10-membered heterocycle, where the heterocycle may be fused to a further 5- to 10-membered ring;

B is a 4- to 8-membered cycloalkyl ring;

and physiologically acceptable salts thereof.

Preference is given, in one embodiment, to compounds of the formula I, in which R1 is H.

Preference is given, in one embodiment, to compounds of the formula I, in which R1 is methyl.

Preference is given, in one embodiment, to compounds of the formula I, in which A is pyrazol-3-yl.

Preference is given, in one embodiment, to compounds of the formula I, in which A is thiazolo[5,4-b]pyridin-2-yl.

Preference is given, in one embodiment, to compounds of the formula I, in which B is cyclopentyl.

Preference is given, in one embodiment, to compounds of the formula I, in which B is cyclohexyl.

Preference is given, in one embodiment, to compounds of the formula I, in which R6 is H.

Preference is given, in one embodiment, to compounds of the formula I, in which R6 is =O.

Preference is given, in one embodiment, to compounds of the formula I, in which R7 is H.

Preference is given, in one embodiment, to compounds of the formula I, in which R4 is —O—($C_1$-$C_6$)-alkyl.

Preference is given, in one embodiment, to compounds of the formula I, in which R4 is $C_1$-$C_6$)-alkyl.

Preference is given, in one embodiment, to compounds of the formula I, in which R4 is benzyl.

The invention relates to compounds of the formula I in the form of their racemates, racemic mixtures and pure enantiomers and also to their diastereomers and mixtures thereof.

If radicals or substituents may be present more than once in the compounds of the formula I, they may all independently of one another have the given meanings and may be identical or different.

The definition ($C_0$-$C_6$)-alkylene- is to be understood as meaning that either a bond or a ($C_1$-$C_6$)-alkylene group may be present.

The definition —($C_0$-$C_6$)-alkyl is to be understood as meaning that either a hydrogen or a ($C_1$-$C_6$)-alkyl group may be present.

"Fusing" or "fused" is to be understood as meaning that a further ring system is fused on. The further fused-on ring system may be aromatic or nonaromatic and carbocyclic or heterocyclic.

Pharmaceutically acceptable salts are, because their solubility in water is greater than that of the initial or basic compounds, particularly suitable for medical applications. These salts must have a pharmaceutically acceptable anion or cation. Suitable pharmaceutically acceptable acid addition salts of the compounds of the invention are salts of inorganic acids such as hydrochloric acid, hydrobromic, phosphoric, metaphosphoric, nitric and sulfuric acids, and organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acids. Suitable pharmaceutically acceptable basic salts are ammonium salts, alkali metal salts (such as sodium and potassium salts), alkaline earth metal salts (such as magnesium and calcium salts), trometamol (2-amino-2-hydroxymethyl-1,3-propanediol), diethanolamine, lysine or ethylenediamine salt.

Salts with a pharmaceutically unacceptable anion such as, for example, trifluoroacetate likewise belong within the framework of the invention as useful intermediates for preparing or purifying pharmaceutically acceptable salts and/or for use in nontherapeutic, for example in vitro applications.

A further aspect of the invention are the physiologically functional derivatives of the compounds of the formula I. The term "physiologically functional derivative" used here refers to all physiologically acceptable derivatives of a compound of the formula I according to the invention, for example an ester, which, when administered to a mammal such as, for example, man is able to form (directly or indirectly) a compound of the formula I or an active metabolite thereof.

The physiologically functional derivatives also include prodrugs of the compounds according to the invention such as, for example, those described in H. Okada et al., Chem. Pharm. Bull. 1994, 42, 57-61. Such prodrugs can be metabolized in vivo to a compound according to the invention. For their part, these prodrugs may be active or not.

The compounds of the invention may also exist in various polymorphous forms, for example as amorphous and crystalline polymorphous forms. All polymorphous forms of the compounds according to the invention belong within the framework of the invention and are a further aspect of the invention.

All references to "compound(s) of formula I" hereinafter refer to compound(s) of the formula I as described hereinabove, and the salts, solvates and physiologically functional derivatives thereof as described herein.

An alkyl radical means a straight-chain or branched hydrocarbon chain having one or more carbons such as, for example, methyl, ethyl, isopropyl, tert-butyl, hexyl.

The alkyl radicals may be mono- or polysubstituted by suitable groups such as, for example: F, Cl, Br, I, $CF_3$, $NO_2$, $N_3$, CN, COOH, COO($C_1$-$C_6$)-alkyl, $CONH_2$, CONH($C_1$-$C_6$)-alkyl, CON[($C_1$-$C_6$)-alkyl]$_2$, cycloalkyl, ($C_2$-$C_6$)-alkenyl, ($C_2$-$C_6$)-alkynyl, O—($C_1$-$C_6$)-alkyl, O—CO—($C_1$-$C_6$)-alkyl, O—CO—($C_1$-$C_6$)-aryl, O—CO—($C_1$-$C_6$)-heterocycle;

$PO_3H_2$, $SO_3H$, $SO_2$—$NH_2$, $SO_2NH$($C_1$-$C_6$)-alkyl, $SO_2N$[($C_1$-$C_6$)-alkyl]$_2$, S—($C_1$-$C_6$)-alkyl, S—($CH_2$)$_n$-aryl, S—($CH_2$)$_n$-heterocycle, SO—($C_1$-$C_6$)-alkyl, SO—($CH_2$)$_n$-aryl, SO—($CH_2$)$_n$-heterocycle, $SO_2$—($C_1$-$C_6$)-alkyl, $SO_2$—($CH_2$)$_n$-aryl, $SO_2$—($CH_2$)$_n$-heterocycle, $SO_2$—NH($CH_2$)$_n$-aryl, $SO_2$—NH($CH_2$)$_n$-heterocycle, $SO_2$—N(($C_1$-$C_6$)-alkyl)($CH_2$)$_n$-aryl, $SO_2$—N(($C_1$-$C_6$)-alkyl)($CH_2$)$_n$-heterocycle, $SO_2$—N(($CH_2$)$_n$-aryl)$_2$, $SO_2$—N(($CH_2$)$_n$-heterocycle)$_2$ where n=0-6 and where the aryl radical or the heterocyclic radical may be substituted up to two times by F, Cl, Br, OH, $CF_3$, $NO_2$, CN, $OCF_3$, O—($C_1$-$C_6$)-alkyl, ($C_1$-$C_6$)-alkyl, $NH_2$;

C(NH)($NH_2$), $NH_2$, NH—($C_1$-$C_6$)-alkyl, N(($C_1$-$C_6$)-alkyl)$_2$, NH($C_2$-$C_7$)-acyl, NH—CO—($C_1$-$C_6$)-alkyl, NH—COO—($C_1$-$C_6$)-alkyl, NH—CO-aryl, NH—CO-heterocycle, NH—COO-aryl, NH—COO-heterocycle, NH—CO—NH—($C_1$-$C_6$)-alkyl, NH—CO—NH-aryl, NH—CO—NH-heterocycle, N[($C_1$-$C_6$)-alkyl]-CO—($C_1$-$C_6$)-alkyl, N[($C_1$-$C_6$)-alkyl]-COO—($C_1$-$C_6$)-alkyl, N[($C_1$-$C_6$)-alkyl]-CO-aryl, N[($C_1$-$C_6$)-alkyl]-CO-heterocycle, N($C_1$-$C_6$)-alkyl-COO-aryl, N[($C_1$-$C_6$)-alkyl]-COO-heterocycle, N[($C_1$-$C_6$)-alkyl]-CO—NH—($C_1$-$C_6$)-alkyl), N[($C_1$-$C_6$)-alkyl]-CO—NH-aryl, N[($C_1$-$C_6$)-alkyl]-CO—NH-heterocycle, N[($C_1$-$C_6$)-alkyl]-CO—N—[($C_1$-$C_6$)-alkyl]$_2$, N[($C_1$-$C_6$)-alkyl]-CO—N[($C_1$-$C_6$)-alkyl)]-aryl, N[($C_1$-$C_6$)-alkyl]-CO—N[($C_1$-$C_6$)-alkyl]-heterocycle, N[($C_1$-$C_6$)-alkyl]-CO—N-(aryl)$_2$, N[($C_1$-$C_6$)-alkyl]-CO—N-(heterocycle)$_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl), N(heterocycle)-CO—NH—($C_1$-$C_6$)-alkyl, N(aryl)-CO—NH-aryl, N(heterocycle)-CO—NH-aryl, N(aryl)-CO—N—[($C_1$-$C_6$)-alkyl]$_2$, N(heterocycle)-CO—N—[($C_1$-$C_6$)-alkyl]$_2$, N(aryl)-CO—N[($C_1$-$C_6$)-alkyl]-aryl, N(heterocycle)-CO—N[($C_1$-$C_6$)-alkyl]-aryl, N(aryl)-CO—N-(aryl)$_2$, N(heterocycle)-

CO—N-(aryl)$_2$, aryl, O—(CH$_2$)$_n$-aryl, O—(CH$_2$)$_n$-heterocycle, where n=0-6 and where the aryl radical or heterocyclic radical may be mono- to trisubstituted by F, Cl, Br, I, OH, CF$_3$, NO$_2$, CN, OCF$_3$, O—(C$_1$-C$_6$)-alkyl, (C$_1$-C$_6$)-alkyl, NH$_2$, NH(C$_1$-C$_6$)-alkyl, N[(C$_1$-C$_6$)-alkyl]$_2$, SO$_2$—CH$_3$, COOH, COO—(C$_1$-C$_6$)-alkyl or CONH$_2$.

An alkenyl radical is to be understood as meaning a straight-chain or branched hydrocarbon chain having two or more carbons and also one or more double bonds such as, for example, vinyl, allyl, pentenyl.

The alkenyl radicals may be mono- or polysubstituted by suitable groups such as, for example: F, Cl, Br, I, CF$_3$, NO$_2$, N$_3$, CN, COOH, COO(C$_1$-C$_6$)-alkyl, CONH$_2$, CONH(C$_1$-C$_6$)-alkyl, CON[(C$_1$-C$_6$)-alkyl]$_2$, cycloalkyl, (C$_2$-C$_6$)-alkenyl, (C$_2$-C$_6$)-alkynyl, O—(C$_1$-C$_6$)-alkyl, O—CO—(C$_1$-C$_6$)-alkyl, O—CO—(C$_1$-C$_6$)-aryl, O—CO—(C$_1$-C$_6$)-heterocycle;

PO$_3$H$_2$, SO$_3$H, SO$_2$—NH$_2$, SO$_2$NH(C$_1$-C$_6$)-alkyl, SO$_2$N[(C$_1$-C$_6$)-alkyl]$_2$, S—(C$_1$-C$_6$)-alkyl, S—(CH$_2$)$_n$-aryl, S—(CH$_2$)$_n$-heterocycle, SO—(C$_1$-C$_6$)-alkyl, SO—(CH$_2$)$_n$-aryl, SO—(CH$_2$)$_n$-heterocycle, SO$_2$—(C$_1$-C$_6$)-alkyl, SO$_2$—(CH$_2$)$_n$-aryl, SO$_2$—(CH$_2$)$_n$-heterocycle, SO$_2$—NH(CH$_2$)$_n$-aryl, SO$_2$—NH(CH$_2$)$_n$-heterocycle, SO$_2$—N((C$_1$-C$_6$)-alkyl)(CH$_2$)$_n$-aryl, SO$_2$—N((C$_1$-C$_6$)-alkyl)(CH$_2$)$_n$-heterocycle, SO$_2$—N((CH$_2$)$_n$-aryl)$_2$, SO$_2$—N((CH$_2$)$_n$-heterocycle)$_2$ where n=0-6 and where the aryl radical or the heterocyclic radical may be substituted up to two times by F, Cl, Br, OH, CF$_3$, NO$_2$, CN, OCF$_3$, O—(C$_1$-C$_6$)-alkyl, (C$_1$-C$_6$)-alkyl, NH$_2$;

C(NH)(NH$_2$), NH$_2$, NH—(C$_1$-C$_6$)-alkyl, N((C$_1$-C$_6$)-alkyl)$_2$, NH(C$_2$-C$_7$)-acyl, NH—CO—(C$_1$-C$_6$)-alkyl, NH—COO—(C$_1$-C$_6$)-alkyl, NH—CO-aryl, NH—CO-heterocycle, NH—COO-aryl, NH—COO-heterocycle, NH—CO—NH—(C$_1$-C$_6$)-alkyl, NH—CO—NH-aryl, NH—CO—NH-heterocycle, N[(C$_1$-C$_6$)-alkyl]-CO—(C$_1$-C$_6$)-alkyl, N[(C$_1$-C$_6$)-alkyl]-COO—(C$_1$-C$_6$)-alkyl, N[(C$_1$-C$_6$)-alkyl]-CO-aryl, N[(C$_1$-C$_6$)-alkyl]-CO-heterocycle, N(C$_1$-C$_6$)-alkyl-COO-aryl, N[(C$_1$-C$_6$)-alkyl]-COO-heterocycle, N[(C$_1$-C$_6$)-alkyl]-CO—NH—(C$_1$-C$_6$)-alkyl), N[(C$_1$-C$_6$)-alkyl]-CO—NH-aryl, N[(C$_1$-C$_6$)-alkyl]-CO—NH-heterocycle, N[(C$_1$-C$_6$)-alkyl]-CO—N—[(C$_1$-C$_6$)-alkyl]$_2$, N[(C$_1$-C$_6$)-alkyl]-CO—N[(C$_1$-C$_6$)-alkyl)]-aryl, N[(C$_1$-C$_6$)-alkyl]-CO—N[(C$_1$-C$_6$)-alkyl]-heterocycle, N[(C$_1$-C$_6$)-alkyl]-CO—N-(aryl)$_2$, N[(C$_1$-C$_6$)-alkyl]-CO—N-(heterocycle)$_2$, N(aryl)-CO—(C$_1$-C$_6$)-alkyl, N(heterocycle)-CO—(C$_1$-C$_6$)-alkyl, N(aryl)-COO—(C$_1$-C$_6$)-alkyl, N(heterocycle)-COO—(C$_1$-C$_6$)-alkyl, N(aryl)-CO-aryl, N(heterocycle)-CO-aryl, N(aryl)-COO-aryl, N(heterocycle)-COO-aryl, N(aryl)-CO—NH—(C$_1$-C$_6$)-alkyl), N(heterocycle)-CO—NH—(C$_1$-C$_6$)-alkyl, N(aryl)-CO—NH-aryl, N(heterocycle)-CO—NH-aryl, N(aryl)-CO—N—[(C$_1$-C$_6$)-alkyl]$_2$, N(heterocycle)-CO—N—[(C$_1$-C$_6$)-alkyl]$_2$, N(aryl)-CO—N[(C$_1$-C$_6$)-alkyl]-aryl, N(heterocycle)-CO—N[(C$_1$-C$_6$)-alkyl]-aryl, N(aryl)-CO—N-(aryl)$_2$, N(heterocycle)-CO—N-(aryl)$_2$, aryl, O—(CH$_2$)$_n$-aryl, O—(CH$_2$)$_n$-heterocycle, where n=0-6 and where the aryl radical or heterocyclic radical may be mono- to trisubstituted by F, Cl, Br, I, OH, CF$_3$, NO$_2$, CN, OCF$_3$, O—(C$_1$-C$_6$)-alkyl, (C$_1$-C$_6$)-alkyl, NH$_2$, NH(C$_1$-C$_6$)-alkyl, N[(C$_1$-C$_6$)-alkyl]$_2$, SO$_2$—CH$_3$, COOH, COO—(C$_1$-C$_6$)-alkyl or CONH$_2$.

An alkynyl radical is to be understood as meaning a straight-chain or branched hydrocarbon chain having two or more carbons and also one or more triple bonds such as, for example, ethynyl, propynyl, hexynyl.

The alkynyl radicals may be mono- or polysubstituted by suitable groups such as, for example: F, Cl, Br, I, CF$_3$, NO$_2$, N$_3$, CN, COOH, COO(C$_1$-C$_6$)-alkyl, CONH$_2$, CONH(C$_1$-C$_6$)-alkyl, CON[(C$_1$-C$_6$)-alkyl]$_2$, cycloalkyl, (C$_2$-C$_6$)-alkenyl, (C$_2$-C$_6$)-alkynyl, O—(C$_1$-C$_6$)-alkyl, O—CO—(C$_1$-C$_6$)-alkyl, O—CO—(C$_1$-C$_6$)-aryl, O—CO—(C$_1$-C$_6$)-heterocycle;

PO$_3$H$_2$, SO$_3$H, SO$_2$—NH$_2$, SO$_2$NH(C$_1$-C$_6$)-alkyl, SO$_2$N[(C$_1$-C$_6$)-alkyl]$_2$, S—(C$_1$-C$_6$)-alkyl, S—(CH$_2$)$_n$-aryl, S—(CH$_2$)$_n$-heterocycle, SO—(C$_1$-C$_6$)-alkyl, SO—(CH$_2$)$_n$-aryl, SO—(CH$_2$)$_n$-heterocycle, SO$_2$—(C$_1$-C$_6$)-alkyl, SO$_2$—(CH$_2$)$_n$-aryl, SO$_2$—(CH$_2$)$_n$-heterocycle, SO$_2$—NH(CH$_2$)$_n$-aryl, SO$_2$—NH(CH$_2$)$_n$-heterocycle, SO$_2$—N((C$_1$-C$_6$)-alkyl)(CH$_2$)$_n$-aryl, SO$_2$—N((C$_1$-C$_6$)-alkyl)(CH$_2$)$_n$-heterocycle, SO$_2$—N((CH$_2$)$_n$-aryl)$_2$, SO$_2$—N((CH$_2$)$_n$-heterocycle)$_2$ where n=0-6 and where the aryl radical or the heterocyclic radical may be substituted up to two times by F, Cl, Br, OH, CF$_3$, NO$_2$, CN, OCF$_3$, O—(C$_1$-C$_6$)-alkyl, (C$_1$-C$_6$)-alkyl, NH$_2$;

C(NH)(NH$_2$), NH$_2$, NH—(C$_1$-C$_6$)-alkyl, N((C$_1$-C$_6$)-alkyl)$_2$, NH(C$_2$-C$_7$)-acyl, NH—CO—(C$_1$-C$_6$)-alkyl, NH—COO—(C$_1$-C$_6$)-alkyl, NH—CO-aryl, NH—CO-heterocycle, NH—COO-aryl, NH—COO-heterocycle, NH—CO—NH—(C$_1$-C$_6$)-alkyl, NH—CO—NH-aryl, NH—CO—NH-heterocycle, N[(C$_1$-C$_6$)-alkyl]-CO—(C$_1$-C$_6$)-alkyl, N[(C$_1$-C$_6$)-alkyl]-COO—(C$_1$-C$_6$)-alkyl, N[(C$_1$-C$_6$)-alkyl]-CO-aryl, N[(C$_1$-C$_6$)-alkyl]-CO-heterocycle, N(C$_1$-C$_6$)-alkyl-COO-aryl, N[(C$_1$-C$_6$)-alkyl]-COO-heterocycle, N[(C$_1$-C$_6$)-alkyl]-CO—NH—(C$_1$-C$_6$)-alkyl), N[(C$_1$-C$_6$)-alkyl]-CO—NH-aryl, N[(C$_1$-C$_6$)-alkyl]-CO—NH-heterocycle, N[(C$_1$-C$_6$)-alkyl]-CO—N—[(C$_1$-C$_6$)-alkyl]$_2$, N[(C$_1$-C$_6$)-alkyl]-CO—N[(C$_1$-C$_6$)-alkyl]-aryl, N[(C$_1$-C$_6$)-alkyl]-CO—N[(C$_1$-C$_6$)-alkyl]-heterocycle, N[(C$_1$-C$_6$)-alkyl]-CO—N-(aryl)$_2$, N[(C$_1$-C$_6$)-alkyl]-CO—N-(heterocycle)$_2$, N(aryl)-CO—(C$_1$-C$_6$)-alkyl, N(heterocycle)-CO—(C$_1$-C$_6$)-alkyl, N(aryl)-COO—(C$_1$-C$_6$)-alkyl, N(heterocycle)-COO—(C$_1$-C$_6$)-alkyl, N(aryl)-CO-aryl, N(heterocycle)-CO-aryl, N(aryl)-COO-aryl, N(heterocycle)-COO-aryl, N(aryl)-CO—NH—(C$_1$-C$_6$)-alkyl), N(heterocycle)-CO—NH—(C$_1$-C$_6$)-alkyl, N(aryl)-CO—NH-aryl, N(heterocycle)-CO—NH-aryl, N(aryl)-CO—N—[(C$_1$-C$_6$)-alkyl]$_2$, N(heterocycle)-CO—N—[(C$_1$-C$_6$)-alkyl]$_2$, N(aryl)-CO—N[(C$_1$-C$_6$)-alkyl]-aryl, N(heterocycle)-CO—N[(C$_1$-C$_6$)-alkyl]-aryl, N(aryl)-CO—N-(aryl)$_2$, N(heterocycle)-CO—N-(aryl)$_2$, aryl, O—(CH$_2$)$_n$-aryl, O—(CH$_2$)$_n$-heterocycle, where n=0-6 and where the aryl radical or heterocyclic radical may be mono- to trisubstituted by F, Cl, Br, I, OH, CF$_3$, NO$_2$, CN, OCF$_3$, O—(C$_1$-C$_6$)-alkyl, (C$_1$-C$_6$)-alkyl, NH$_2$, NH(C$_1$-C$_6$)-alkyl, N[(C$_1$-C$_6$)-alkyl]$_2$, SO$_2$—CH$_3$, COOH, COO—(C$_1$-C$_6$)-alkyl or CONH$_2$.

An aryl radical is to be understood as meaning a phenyl, naphthyl, biphenyl, tetrahydronaphthyl, alpha- or beta-tetralone, indanyl- or indan-1-onyl radical.

The aryl radicals may be mono- or polysubstituted by suitable groups such as, for example: F, Cl, Br, I, CF$_3$, NO$_2$, N$_3$, CN, COOH, COO(C$_1$-C$_6$)-alkyl, CONH$_2$, CONH(C$_1$-C$_6$)-alkyl, CON[(C$_1$-C$_6$)-alkyl]$_2$, cycloalkyl, (C$_2$-C$_6$)-alkenyl, (C$_2$-C$_6$)-alkynyl, O—(C$_1$-C$_6$)-alkyl, O—CO—(C$_1$-C$_6$)-alkyl, O—CO—(C$_1$-C$_6$)-aryl, O—CO—(C$_1$-C$_6$)-heterocycle;

PO$_3$H$_2$, SO$_3$H, SO$_2$—NH$_2$, SO$_2$NH(C$_1$-C$_6$)-alkyl, SO$_2$N[(C$_1$-C$_6$)-alkyl]$_2$, S—(C$_1$-C$_6$)-alkyl, S—(CH$_2$)$_n$-aryl, S—(CH$_2$)$_n$-heterocycle, SO—(C$_1$-C$_6$)-alkyl, SO—(CH$_2$)$_n$-aryl, SO—(CH$_2$)$_n$-heterocycle, SO$_2$—(C$_1$-C$_6$)-alkyl, SO$_2$—(CH$_2$)$_n$-aryl, SO$_2$—(CH$_2$)$_n$-heterocycle, SO$_2$—NH(CH$_2$)$_n$-aryl, SO$_2$—NH(CH$_2$)$_n$-heterocycle, SO$_2$—N((C$_1$-C$_6$)-alkyl)(CH$_2$)$_n$-aryl, SO$_2$—N((C$_1$-C$_6$)-alkyl)(CH$_2$)$_n$-heterocycle, SO$_2$—N((CH$_2$)$_n$-aryl)$_2$, SO$_2$—N((CH$_2$)$_n$-heterocycle)$_2$ where n=0-6 and where the aryl radical or the heterocyclic radical may be substituted up to two times by F, Cl, Br, OH, CF$_3$, NO$_2$, CN, OCF$_3$, O—(C$_1$-C$_6$)-alkyl, (C$_1$-C$_6$)-alkyl, NH$_2$;

C(NH)(NH$_2$), NH$_2$, NH—(C$_1$-C$_6$)-alkyl, N((C$_1$-C$_6$)-alkyl)$_2$, NH(C$_2$-C$_7$)-acyl, NH—CO—(C$_1$-C$_6$)-alkyl, NH—COO—(C$_1$-C$_6$)-alkyl, NH—CO-aryl, NH—CO-heterocycle, NH—COO-aryl, NH—COO-heterocycle, NH—CO—NH—(C$_1$-C$_6$)-alkyl, NH—CO—NH-aryl, NH—CO—NH-heterocycle, N[(C$_1$-C$_6$)-alkyl]-CO—(C$_1$-C$_6$)-alkyl, N[(C$_1$-C$_6$)-alkyl]-COO—(C$_1$-C$_6$)-alkyl, N[(C$_1$-C$_6$)-alkyl]-CO-aryl, N[(C$_1$-C$_6$)-alkyl]-CO-heterocycle, N(C$_1$-C$_6$)-alkyl-COO-aryl, N[(C$_1$-C$_6$)-alkyl]-COO-heterocycle, N[(C$_1$-C$_6$)-alkyl]-CO—NH—(C$_1$-C$_6$)-alkyl, N[(C$_1$-C$_6$)-alkyl]-CO—NH-aryl, N[(C$_1$-C$_6$)-alkyl]-CO—NH-heterocycle, N[(C$_1$-C$_6$)-alkyl]-CO—N—[(C$_1$-C$_6$)-alkyl]$_2$, N[(C$_1$-C$_6$)-alkyl]-CO—N[(C$_1$-C$_6$)-alkyl)]-aryl, N[(C$_1$-C$_6$)-alkyl]-CO—N[(C$_1$-C$_6$)-alkyl]-heterocycle, N[(C$_1$-C$_6$)-alkyl]-CO—N-(aryl)$_2$, N[(C$_1$-C$_6$)-alkyl]-CO—N-(heterocycle)$_2$, N(aryl)-CO—(C$_1$-C$_6$)-alkyl, N(heterocycle)-CO—(C$_1$-C$_6$)-alkyl, N(aryl)-COO—(C$_1$-C$_6$)-alkyl, N(heterocycle)-COO—(C$_1$-C$_6$)-alkyl, N(aryl)-CO-aryl, N(heterocycle)-CO-aryl, N(aryl)-COO-aryl, N(heterocycle)-COO-aryl, N(aryl)-CO—NH—(C$_1$-C$_6$)-alkyl), N(heterocycle)-CO—NH—(C$_1$-C$_6$)-alkyl, N(aryl)-CO—NH-aryl, N(heterocycle)-CO—NH-aryl, N(aryl)-CO—N—[(C$_1$-C$_6$)-alkyl]$_2$, N(heterocycle)-CO—N—[(C$_1$-C$_6$)-alkyl]$_2$, N(aryl)-CO—N[(C$_1$-C$_6$)-alkyl]-aryl, N(heterocycle)-CO—N[(C$_1$-C$_6$)-alkyl]-aryl, N(aryl)-CO—N-(aryl)$_2$, N(heterocycle)-CO—N-(aryl)$_2$, aryl, O—(CH$_2$)$_n$-aryl, O—(CH$_2$)$_n$-heterocycle, where n=0-6 and where the aryl radical or heterocyclic radical may be mono- to trisubstituted by F, Cl, Br, I, OH, CF$_3$, NO$_2$, CN, OCF$_3$, O—(C$_1$-C$_6$)-alkyl, (C$_1$-C$_6$)-alkyl, NH$_2$, NH(C$_1$-C$_6$)-alkyl, N[(C$_1$-C$_6$)-alkyl]$_2$, SO$_2$—CH$_3$, COOH, COO—(C$_1$-C$_6$)-alkyl or CONH$_2$.

A cycloalkyl radical is to be understood as meaning a ring system which comprises one or more rings and is saturated or partially unsaturated (with one or two double bonds) and is constructed exclusively of carbon atoms, such as, for example, cyclopropyl, cyclopentyl, cyclopentenyl, cyclohexyl or adamantyl.

The cycloalkyl radicals may be mono- or polysubstituted by suitable groups such as, for example: F, Cl, Br, I, CF$_3$, NO$_2$, N$_3$, CN, COOH, COO(C$_1$-C$_6$)-alkyl, CONH$_2$, CONH(C$_1$-C$_6$)-alkyl, CON[(C$_1$-C$_6$)-alkyl]$_2$, cycloalkyl, (C$_2$-C$_6$)-alkenyl, (C$_2$-C$_6$)-alkynyl, O—(C$_1$-C$_6$)-alkyl, O—CO—(C$_1$-C$_6$)-alkyl, O—CO—(C$_1$-C$_6$)-aryl, O—CO—(C$_1$-C$_6$)-heterocycle, PO$_3$H$_2$, SO$_3$H, SO$_2$—NH$_2$, SO$_2$NH(C$_1$-C$_6$)-alkyl, SO$_2$N[(C$_1$-C$_6$)-alkyl]$_2$, S—(C$_1$-C$_6$)-alkyl, S—(CH$_2$)$_n$-aryl, S—(CH$_2$)$_n$-heterocycle, SO—(C$_1$-C$_6$)-alkyl, SO—(CH$_2$)$_n$-aryl, SO—(CH$_2$)$_n$-heterocycle, SO$_2$—(C$_1$-C$_6$)-alkyl, SO$_2$—(CH$_2$)$_n$-aryl, SO$_2$—(CH$_2$)$_n$-heterocycle, SO$_2$—NH(CH$_2$)$_n$-aryl, SO$_2$—NH(CH$_2$)$_n$-heterocycle, SO$_2$—N((C$_1$-C$_6$)-alkyl)(CH$_2$)$_n$-aryl, SO$_2$—N((C$_1$-C$_6$)-alkyl)(CH$_2$)$_n$-heterocycle, SO$_2$—N((CH$_2$)$_n$-aryl)$_2$, SO$_2$—N((CH$_2$)$_n$-heterocycle)$_2$ where n=0-6 and where the aryl radical or the heterocyclic radical may be substituted up to two times by F, Cl, Br, OH, CF$_3$, NO$_2$, CN, OCF$_3$, O—(C$_1$-C$_6$)-alkyl, (C$_1$-C$_6$)-alkyl, NH$_2$;

C(NH)(NH$_2$), NH$_2$, NH—(C$_1$-C$_6$)-alkyl, N((C$_1$-C$_6$)-alkyl)$_2$, NH(C$_2$-C$_7$)-acyl, NH—CO—(C$_1$-C$_6$)-alkyl, NH—COO—(C$_1$-C$_6$)-alkyl, NH—CO-aryl, NH—CO-heterocycle, NH—COO-aryl, NH—COO-heterocycle, NH—CO—NH—(C$_1$-C$_6$)-alkyl, NH—CO—NH-aryl, NH—CO—NH-heterocycle, N[(C$_1$-C$_6$)-alkyl]-CO—(C$_1$-C$_6$)-alkyl, N[(C$_1$-C$_6$)-alkyl]-COO—(C$_1$-C$_6$)-alkyl, N[(C$_1$-C$_6$)-alkyl]-CO-aryl, N[(C$_1$-C$_6$)-alkyl]-CO-heterocycle, N(C$_1$-C$_6$)-alkyl-COO-aryl, N[(C$_1$-C$_6$)-alkyl]-COO-heterocycle, N[(C$_1$-C$_6$)-alkyl]-CO—NH—(C$_1$-C$_6$)-alkyl), N[(C$_1$-C$_6$)-alkyl]-CO—NH-aryl, N[(C$_1$-C$_6$)-alkyl]-CO—NH-heterocycle, N[(C$_1$-C$_6$)-alkyl]-CO—N—[(C$_1$-C$_6$)-alkyl]$_2$, N[(C$_1$-C$_6$)-alkyl]-CO—N[(C$_1$-C$_6$)-alkyl)]-aryl, N[(C$_1$-C$_6$)-alkyl]-CO—N-(aryl)$_2$, N[(C$_1$-C$_6$)-alkyl]-CO—N-(heterocycle)$_2$, N(aryl)-CO—(C$_1$-C$_6$)-alkyl, N(heterocycle)-CO—(C$_1$-C$_6$)-alkyl, N(aryl)-COO—(C$_1$-C$_6$)-alkyl, N(heterocycle)-COO—(C$_1$-C$_6$)-alkyl, N(aryl)-CO-aryl, N(heterocycle)-CO-aryl, N(aryl)-COO-aryl, N(heterocycle)-COO-aryl, N(aryl)-CO—NH—(C$_1$-C$_6$)-alkyl), N(heterocycle)-CO—NH—(C$_1$-C$_6$)-alkyl, N(aryl)-CO—NH-aryl, N(heterocycle)-CO—NH-aryl, N(aryl)-CO—N—[(C$_1$-C$_6$)-alkyl]$_2$, N(heterocycle)-CO—N—[(C$_1$-C$_6$)-alkyl]$_2$, N(aryl)-CO—N[(C$_1$-C$_6$)-alkyl]-aryl, N(heterocycle)-CO—N[(C$_1$-C$_6$)-alkyl]-aryl, N(aryl)-CO—N-(aryl)$_2$, N(heterocycle)-CO—N-(aryl)$_2$, aryl, O—(CH$_2$)$_n$-aryl, O—(CH$_2$)$_n$-heterocycle, where n=0-6 and where the aryl radical or the heterocyclic radical may be mono- to trisubstituted by F, Cl, Br, I, OH, CF$_3$, NO$_2$, CN, OCF$_3$, O—(C$_1$-C$_6$)-alkyl, (C$_1$-C$_6$)-alkyl, NH$_2$, NH(C$_1$-C$_6$)-alkyl, N[(C$_1$-C$_6$)-alkyl]$_2$, SO$_2$—CH$_3$, COOH, COO—(C$_1$-C$_6$)-alkyl or CONH$_2$.

A heterocycle or heterocyclic radical is to be understood as meaning rings and ring systems which, in addition to carbon, also contain heteroatoms, such as, for example, nitrogen, oxygen or sulfur. This definition furthermore includes ring systems in which the heterocycle or the heterocyclic radical is fused to a further ring system.

Suitable "heterocycles" or "heterocyclic radicals" are acridinyl, azocinyl, benzimidazolyl, benzofuryl, benzothienyl, benzothiophenyl, benzoxazolyl, benzothiazolyl, benzotriazolyl, benzotetrazolyl, benzisoxazolyl, benzisothiazolyl, benzimidazalinyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, 2H,6H-1,5,2-dithiazinyl, dihydrofuro[2,3-b]-tetrahydrofuran, 5,6-dihydro-4H-cyclopentathiazol-2-yl, 4,5-dihydrothiazol-2-yl, furyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, 4,5,6,7-tetrahydrobenzoxazol-2-yl, 4,5,6,7-tetrahydro-benzothiazol-2-yl, 4,5,6,7-tetrahydrobenzimidazol-2-yl, 4,5,6,7-tetrahydro-pyrazolo[1,5-a]pyridin-2-yl, tetrahydrofuranyl, tetrahydropyranyl, tetrahydroisoquinolinyl, tetrahydroquinolinyl, 6H-1,2,5-thiadazinyl, thiazolyl, 1,2,3-thiadiazolyl, 1,2,4-thiadiazolyl, 1,2,5-thiadiazolyl, 1,3,4-thiadiazolyl, thienyl, triazinyl, triazolyl, tetrazolyl, thiazolo[4,5-b]pyridinyl, thieno[2,3-d]thiazol-2-yl and xanthenyl.

Pyridyl denotes both 2-, 3- and 4-pyridyl. Thienyl denotes both 2- and 3-thienyl. Furyl denotes both 2- and 3-furyl.

Also included are the corresponding N-oxides of these compounds, i.e., for example, 1-oxy-2-, 3- or 4-pyridyl.

Furthermore included are mono- or polybenzo-fused derivatives of these heterocycles.

The heterocycles or heterocyclic radicals may be mono- or polysubstituted by suitable groups such as, for example: F, Cl, Br, I, $CF_3$, $NO_2$, $N_3$, CN, COOH, COO($C_1$-$C_6$)-alkyl, $CONH_2$, CONH($C_1$-$C_6$)-alkyl, CON[($C_1$-$C_6$)-alkyl]$_2$, cycloalkyl, ($C_2$-$C_6$)-alkenyl, ($C_2$-$C_6$)-alkynyl, O—($C_1$-$C_6$)-alkyl, O—CO—($C_1$-$C_6$)-aryl, O—CO—($C_1$-$C_6$)-heterocycle;

$PO_3H_2$, $SO_3H$, $SO_2$—$NH_2$, $SO_2NH$($C_1$-$C_6$)-alkyl, $SO_2N$[($C_1$-$C_6$)-alkyl]$_2$, S—($C_1$-$C_6$)-alkyl, S—($CH_2$)$_n$-aryl, S—($CH_2$)$_n$-heterocycle, SO—($C_1$-$C_6$)-alkyl, SO—($CH_2$)$_n$-aryl, SO—($CH_2$)$_n$-heterocycle, $SO_2$—($C_1$-$C_6$)-alkyl, $SO_2$—($CH_2$)$_n$-aryl, $SO_2$—($CH_2$)$_n$-heterocycle, $SO_2$—NH($CH_2$)$_n$-aryl, $SO_2$—NH($CH_2$)$_n$-heterocycle, $SO_2$—N($C_1$-$C_6$)-alkyl)($CH_2$)$_n$-aryl, $SO_2$—N($C_1$-$C_6$)-alkyl)($CH_2$)$_n$-heterocycle, $SO_2$—N(($CH_2$)$_n$-aryl)$_2$, $SO_2$—N(($CH_2$)$_n$-(heterocycle)$_2$ where n=0-6 and where the aryl radical or the heterocyclic radical may be substituted up to two times by F, Cl, Br, OH, $CF_3$, $NO_2$, CN, $OCF_3$, O—($C_1$-$C_6$)-alkyl, ($C_1$-$C_6$)-alkyl, $NH_2$;

C(NH)($NH_2$), $NH_2$, NH—($C_1$-$C_6$)-alkyl, N(($C_1$-$C_6$)-alkyl)$_2$, NH($C_2$-$C_7$)-acyl, NH—CO—($C_1$-$C_6$)-alkyl, NH—COO—($C_1$-$C_6$)-alkyl, NH—CO-aryl, NH—CO-heterocycle, NH—COO-aryl, NH—COO-heterocycle, NH—CO—NH—($C_1$-$C_6$)-alkyl, NH—CO—NH-aryl, NH—CO—NH-heterocycle, N[($C_1$-$C_6$)-alkyl]-CO—($C_1$-$C_6$)-alkyl, N[($C_1$-$C_6$)-alkyl]-COO—($C_1$-$C_6$)-alkyl, N[($C_1$-$C_6$)-alkyl]-CO-aryl, N[($C_1$-$C_6$)-alkyl]-CO-heterocycle, N($C_1$-$C_6$)-alkyl-COO-aryl, N[($C_1$-$C_6$)-alkyl]-COO-heterocycle, N[($C_1$-$C_6$)-alkyl]-CO—NH—($C_1$-$C_6$)-alkyl), N[($C_1$-$C_6$)-alkyl]-CO—NH-aryl, N[($C_1$-$C_6$)-alkyl]-CO—NH-heterocycle, N[($C_1$-$C_6$)-alkyl]-CO—N—[($C_1$-$C_6$)-alkyl]$_2$, N[($C_1$-$C_6$)-alkyl]-CO—N[($C_1$-$C_6$)-alkyl)]-aryl, N[($C_1$-$C_6$)-alkyl]-CO—N[($C_1$-$C_6$)-alkyl]-heterocycle, N[($C_1$-$C_6$)-alkyl]-CO—N-(aryl)$_2$, N[($C_1$-$C_6$)-alkyl]-CO—N-(heterocycle)$_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl), N(heterocycle)-CO—NH—($C_1$-$C_6$)-alkyl, N(aryl)-CO—NH-aryl, N(heterocycle)-CO—NH-aryl, N(aryl)-CO—N—[($C_1$-$C_6$)-alkyl]$_2$, N(heterocycle)-CO—N—[($C_1$-$C_6$)-alkyl]$_2$, N(aryl)-CO—N[($C_1$-$C_6$)-alkyl]-aryl, N(heterocycle)-CO—N[($C_1$-$C_6$)-alkyl]-aryl, N(aryl)-CO—N-(aryl)$_2$, N(heterocycle)-CO—N-(aryl)$_2$, aryl, O—($CH_2$)$_n$-aryl, O—($CH_2$)$_n$-heterocycle, where n=0-6 and where the aryl radical or the heterocyclic radical may be mono- to trisubstituted by F, Cl, Br, I, OH, $CF_3$, $NO_2$, CN, $OCF_3$, O—($C_1$-$C_6$)-alkyl, ($C_1$-$C_6$)-alkyl, $NH_2$, NH($C_1$-$C_6$)-alkyl, N[($C_1$-$C_6$)-alkyl]$_2$, $SO_2$—$CH_3$, COOH, COO—($C_1$-$C_6$)-alkyl or $CONH_2$.

Compounds of the formula I activate glucose metabolism in glucokinase-expressing cells. They are therefore highly suitable for treating and preventing elevated blood glucose levels, obesity and metabolic syndrome (Sagen et al. Diabetes 55, 1713-1722, Levin et al. Diabetes (2006), S122-S130, Matschinsky et al (2006) 55, 1-12).

By virtue of the fact that they activate glucokinase, the compounds of the formula I may also be suitable for treating or preventing further diseases and conditions caused by elevated blood glucose levels, obesity or by reduced glucokinase activity in a mammal, preferably a human.

The compounds of the present invention are suitable in particular for the treatment and/or prevention of:

1. Glucose utilization disorders and disorders of fatty acid metabolism
   disorders associated with insulin resistance
   Diabetes mellitus, in particular type-2 diabetes, including the prevention of sequelae associated therewith.

Particular aspects in this context are
   hyperglycemia,
   improving insulin resistance,
   improving glucose tolerance,
   protection of the β-cells of the pancreas
   prevention of macro- and microvascular disorders 2. Obesity and its sequelae such as, for example, dyslipidemias, atherosclerosis, coronary heart disease, cerebrovascular disorders etc., in particular (but not limited thereto) those with are characterized by one or more of the following factors:
   high plasma triglyceride concentrations, high postprandial plasmatriglyceride concentrations,
   low HDL cholesterol concentration
   low ApoA lipoprotein concentrations
   high LDL cholesterol concentrations
   low LDL cholesterol particles
   high ApoB lipoprotein concentrations 3. Various other conditions which may be associated with metabolic syndrome or syndrome X such as
   increasing waist line
   dyslipidemia (for example hypertriglyceridemia and/or low HDL)
   insulin resistance
   hypercoagulability
   hyperurikemia
   microalbuminemia
   thromboses, hypercoagulable and prothrombotic conditions (arterial and venous)
   hypertension
   heart failure, for example (but not limited thereto) after myocardial infarction, hypertensive heart disease or cardiomyopathy 4. Primary hypertriglyceridemia or secondary hypertriglyceridemias after familiar reticulohistiocytosis
   lipoprotein lipase deficiency
   hyperlipoproteinemias
   apolipoprotein deficiency (for example ApoCII or ApoE deficiency)

5. Genetically reduced activity of glucokinase, in particular MODY2

6. Diseases or conditions associated with neurological, psychiatric or immune disorders or conditions The compound(s) of the formula (I) can also be administered in combination with further active ingredients.

The amount of a compound of formula I necessary to achieve the desired biological effect depends on a number of factors, for example the specific compound chosen, the intended use, the mode of administration and the clinical condition of the patient. The daily dose is generally in the range from 0.3 mg to 100 mg (typically from 3 mg to 50 mg) per day and per kilogram of body weight, for example 3-10 mg/kg/day. An intravenous dose may be for example in the range from 0.3 mg to 1.0 mg/kg, which can suitably be administered as infusion of from 10 ng to 100 ng per kilogram per minute. Suitable infusion solutions for these purposes may comprise for example from 0.1 ng to 100 mg, typically from 1 ng to 100 mg, per milliliter. Single doses may comprise for example from 1 mg to 10 g of the active ingredient. Thus, ampules for injections may comprise for example from 1 mg to 100 mg, and single-dose formulations which can be administered orally, such as, for example, tablets or capsules, may comprise for example from 1.0 to 1000 mg, typically from 10 to 600 mg. For the therapy of the abovementioned conditions, the compounds of formula I may be used as the compound itself, but are preferably in the form of a pharmaceutical composition with an acceptable carrier. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including further compounds of formula I. The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of formula I used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical compounds for oral administration may be in the form of separate units such as, for example, capsules, cachets, suckable tablets or tablets, each of which contains a defined amount of the compound of formula I; as powders or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one (or more) surface-active/dispersing agent(s) in a suitable machine. Molded tablets can be produced by molding the compound, which is in powder form and is moistened with an inert liquid diluent, in a suitable machine.

Pharmaceutical compositions which are suitable for peroral (sublingual) administration comprise suckable tablets which contain a compound of formula I with a flavoring, normally sucrose and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain from 0.1 to 5% by weight of the active compound.

Pharmaceutical compositions suitable for rectal administration are preferably in the form of single-dose suppositories. These can be produced by mixing a compound of the formula I with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Pharmaceutical compositions suitable for transdermal uses can be in the form of single patches which are suitable for long-term close contact with the patient's epidermis. Such patches suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular possibility is for the active ingredient to be released by electrotransport or iontophoresis as described, for example, in Pharmaceutical Research, 2(6): 318 (1986).

Further active ingredients suitable for combination products are:

All antidiabetics which are mentioned in the Rote Liste 2006, chapter 12; all weight-reducing agents/appetite suppressants which are mentioned in the Rote Liste 2006, chapter 1; all lipid-lowering agents which are mentioned in the Rote Liste 2006, chapter 58. They may be combined with the compound of the invention of the formula I in particular for a synergistic improvement in the effect. The active ingredient combination can be administered either by separate administration of the active ingredients to the patient or in the form of combination products in which a plurality of active ingredients is present in a pharmaceutical preparation. Most of the active ingredients mentioned hereinafter are disclosed in the USP Dictionary of USAN and International Drug Names, US Pharmacopeia, Rockville 2001.

Antidiabetics include insulin and insulin derivatives such as, for example, LANTUS® (see www.lantus.com) or HMR 1964 or LEVEMIR® (insulin detemir) or those described in WO2005005477 (Novo Nordisk), fast-acting insulins (see U.S. Pat. No. 6,221,633), inhalable insulins such as, for example, EXUBERA® or oral insulins such as, for example, IN-105 (NOBEX) or ORAL-LYN™ (Generex Biotechnology), GLP-1 derivatives such as, for example, exenatide, liraglutide or those which have been disclosed in WO98/08871, WO2005027978, WO2006037811, WO2006037810 of Novo Nordisk A/S, in WO01/04156 of Zealand or in WO00/34331 of Beaufour-Ipsen, pramlintide acetate (Symlin; Amylin Pharmaceuticals), and orally effective hypoglycemic active ingredients.

The orally effective hypoglycemic active ingredients include preferably sulfonylureas,
  biguanidines,
  meglitinides,
  oxadiazolidinediones,
  thiazolidinediones,
  glucosidase inhibitors,
  inhibitors of glycogen phosphorylase,
  glucagon antagonists,
  glucokinase activators,
  inhibitors of fructose-1,6-bisphosphatase,
  modulators of glucose transporter 4 (GLUT4), inhibitors of glutamine-fructose-6-phosphate amidotransferase (GFAT), GLP-1 agonists, potassium channel openers such as, for example those which have been disclosed in WO 97/26265 and WO 99/03861 of Novo Nordisk A/S or those described in WO2006045799 (Solvay), inhibitors of dipeptidylpeptidase IV (DPP-IV), insulin sensitizers, inhibitors of liver enzymes involved in stimulating gluconeogenesis and/or glycogenolysis, modulators of glucose uptake, of glucose transport and of glucose reabsorption, inhibitors of 11β-HSD1, inhibitors of protein tyrosine phosphatase 1B (PTP1B), modulators of the sodium-dependent glucose transporter 1 or 2 (SGLT1, SGLT2), compounds which alter lipid metabolism such as antihyperlipidemic active ingredients and antilipidemic active ingredients, compounds which reduce food intake, compounds which increase thermogenesis, PPAR and RXR modulators (retinoid X receptor) and active ingredients which act on the ATP-dependent potassium channel of the beta cells.

In one embodiment of the invention, the compound of the formula I is administered in combination with a TR-β agonist (thyroid receptor).

In one embodiment of the invention, the compound of the formula I is administered in combination with an HMGCoA reductase inhibitor (hydroxymethylglutoryl-coenzyme A) such as simvastatin, fluvastatin, pravastatin, lovastatin, atorvastatin, cerivastatin, rosuvastatin, L-659699.

In one embodiment of the invention, the compound of the formula I is administered in combination with a cholesterol absorption inhibitor such as, for example, ezetimibe, tiqueside, pamaqueside, FM-VP4 (sitostanol/campesterol ascorbyl phosphate; Forbes Medi-Tech, WO2005042692, WO2005005453), MD-0727 (Microbia Inc., WO2005021497, WO2005021495) or with compounds as described in WO2002066464 (Kotobuki Pharmaceutical Co. Ltd.) or WO2005044256 or WO2005062824 (Merck & Co.) or WO2005061451 and WO2005061452 (AstraZeneca AB) and WO2006017257 (Phenomix) or WO2005033100 (Lipideon Biotechnology AG).

In one embodiment of the invention, the compound of the formula I is administered in combination with Vytorin™, a fixed combination of ezetimibe with simvastatin.

In one embodiment of the invention, the compound of the formula I is administered in combination with a fixed combination of ezetimibe with fenofibrate.

In a further embodiment of the invention, the compound of the formula I is administered in combination with a fixed combination of fenofibrate with rosuvastatin.

In one embodiment of the invention, the compound of the formula I is administered in combination with ISIS-301012, an antisense oligonucleotide able to regulate the apolipoprotein B gene.

In one embodiment of the invention, the compound of the formula I is administered in combination with a PPAR gamma agonist (peroxisome proliferator-activated receptors) such as, for example, rosiglitazone, pioglitazone, JTT-501, GI 262570, R-483 or CS-011 (rivoglitazone).

In one embodiment of the invention, the compound of the formula I is administered in combination with COMPETACT™, a fixed combination of pioglitazone hydrochloride with metformin hydrochloride.

In one embodiment of the invention, the compound of the formula I is administered in combination with DUETACT™, a fixed combination of pioglitazone hydrochloride with glimepiride.

In one embodiment of the invention, the compound of the formula I is administered in combination with AVANDAMET®, a fixed combination of rosiglitazone maleate with metformin hydrochloride.

In one embodiment of the invention, the compound of the formula I is administered in combination with a PPAR alpha agonist such as, for example, GW9578, GW-590735, K-111, LY-674, KRP-101, DRF-10945.

In one embodiment of the invention, the compound of the formula I is administered in combination with a mixed PPAR alpha/gamma agonist such as, for example, naveglitazar, LY-510929, ONO-5129, E-3030, AVE 8042, AVE 8134, AVE 0847, or as in PCT/US 00/11833, PCT/US 00/11490, DE10142734.4 or as described in J. P. Berger et al., TRENDS in Pharmacological Sciences 28(5), 244-251, 2005.

In one embodiment, the compound of the formula I is administered in combination with a PPAR delta agonist such as, for example, GW-501516.

In one embodiment, the compound of the formula I is administered in combination with metaglidasen or with MBX-2044 or other partial PPAR gamma agonists/antagonists.

In a further embodiment of the invention, the compound of the formula I is administered in combination with an activator of AMP-activated protein kinase (AMPK), such as, for example, A-769662 or those compounds as described in US20050038068.

In one embodiment of the invention, the compound of the formula I is administered in combination with a fibrate such as, for example, fenofibrate, clofibrate, bezafibrate.

In one embodiment of the invention, the compound of the formula I is administered in combination with an MTP inhibitor (microsomal triglyceride transfer protein) such as, for example, implitapide, BMS-201038, R-103757 or those as described in WO2005085226, WO2005121091, WO2006010423.

In one embodiment of the invention, the compound of the formula I is administered in combination with a 5HT agonist (serotonin reuptake).

In one embodiment of the invention, the compound of the formula I is administered in combination with a CETP inhibitor (cholesterol ester transfer protein) such as, for example, torcetrapib or JTT-705 or those as described in WO2006002342, WO2006010422, WO2006012093.

In one embodiment of the invention, the compound of the formula I is administered in combination with a bile acid absorption inhibitor (see, for example, U.S. Pat. No. 6,245,744, U.S. Pat. No. 6,221,897 or WO00/61568) such as, for example, HMR 1741 or those as described in DE 10 2005 033099.1 and DE 10 2005 033100.9.

In one embodiment, the compound of the formula I is administered in combination with a polymeric bile acid adsorbent such as, for example, cholestyramine or colesevelam.

In one embodiment of the invention, the compound of the formula I is administered in combination with an LDL receptor inducer (low-density lipoprotein—see U.S. Pat. No. 6,342,512), such as, for example, HMR1171, HMR1586 or those as described in WO2005097738.

In one embodiment, the compound of the formula I is administered in combination with Omacor® (omega-3 fatty acids; highly concentrated ethyl esters of eicosapentaenoic acid and of docosahexaenoic acid).

In one embodiment of the invention, the compound of the formula I is administered in combination with an ACAT inhibitor (acyl-CoA: cholesterol acyl transferase) such as, for example, avasimibe or SMP-797.

In one embodiment of the invention, the compound of the formula I is administered in combination with an antioxidant such as, for example, OPC-14117, probucol, tocopherol, ascorbic acid, β-carotene or selenium.

In one embodiment of the invention, the compound of the formula I is administered in combination with a vitamin such as, for example, vitamin B6 or vitamin B12.

In one embodiment of the invention, the compound of the formula I is administered in combination with a lipoprotein lipase modulator such as, for example, ibrolipim (NO-1886).

In one embodiment of the invention, the compound of the formula I is administered in combination with an ATP citrate lyase inhibitor (adenosine triphosphate citrate lyase) such as, for example, SB-204990.

In one embodiment of the invention the compound of the formula I is administered in combination with a TNF agonist (tumor necrosis factor).

In one embodiment of the invention, the compound of the formula I is administered in combination with a squalene synthetase inhibitor such as, for example, BMS-188494 or as described in WO2005077907.

In one embodiment of the invention, the compound of the formula I is administered in combination with a lipoprotein (a) antagonist such as, for example, gemcabene (CI-1027).

In one embodiment of the invention, the compound of the formula I is administered in combination with an agonist of GPR109A (HM74A receptor agonist) such as, for example, nicotinic acid or extended release niacin in conjunction with MK-0524A or the compounds described in WO2006045565, WO2006045564, WO2006069242.

In another embodiment of the invention, the compound of the formula I is administered in combination with an agonist of GPR116 as described for example in WO2006067531, WO2006067532.

In one embodiment of the invention, the compound of the formula I is administered in combination with a lipase inhibitor such as, for example, orlistat or cetilistat (ATL-962).

In one embodiment of the invention, the compound of the formula I is administered in combination with insulin.

In one embodiment, the compound of the formula I is administered in combination with a sulfonylurea such as, for example, tolbutamide, glibenclamide, glipizide or glimepiride.

In one embodiment, the compound of the formula I is administered in combination with a substance which enhances insulin secretion, such as, for example, KCP-265 (WO2003097064).

In one embodiment, the compound of the formula I is administered in combination with agonists of the glucose-dependent insulinotropic receptor (GDIR), such as, for example, APD-668.

In one embodiment, the compound of the formula I is administered in combination with a biguanide such as, for example, metformin.

In another embodiment, the compound of the formula I is administered in combination with a meglitinide such as, for example, repaglinide or nateglinide.

In one embodiment, the compound of the formula I is administered in combination with a thiazolidinedione such as, for example, troglitazone, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinyl)methoxy]phenyl]methyl]-2,4-thiazolidinedione.

In one embodiment, the compound of the formula I is administered in combination with an α-glucosidase inhibitor such as, for example, miglitol or acarbose.

In one embodiment, the compound of the formula I is administered in combination with an active ingredient which acts on the ATP-dependent potassium channel of the beta cells, such as, for example, tolbutamide, glibenclamide, glipizide, glimepiride or repaglinide.

In one embodiment, the compound of the formula I is administered in combination with more than one of the aforementioned compounds, for example in combination with a sulfonylurea and metformin, a sulfonylurea and acarbose, repaglinide and metformin, insulin and a sulfonylurea, insulin and metformin, insulin and troglitazone, insulin and lovastatin, etc.

In one embodiment, the compound of the formula I is administered in combination with an inhibitor of glycogen phosphorylase, such as, for example, PSN-357 or FR-258900 or those as described in WO2003084922, WO2004007455, WO2005073229-31, WO2005067932.

In one embodiment, the compound of the formula I is administered in combination with glucagon receptor antagonists such as, for example, A-770077, NNC-25-2504 or as described in WO2004100875 or WO2005065680.

In one embodiment, the compound of the formula I is administered in combination with activators of glucokinase, such as, for example, LY-2121260 (WO2004063179), PSN-105, PSN-110, GKA-50 or those as are described, for example, in WO2004072031, WO2004072066, WO2005080360, WO2005044801, WO2006016194, WO2006058923.

In one embodiment, the compound of the formula I is administered in combination with an inhibitor of gluconeogenesis, such as, for example, FR-225654.

In one embodiment, the compound of the formula I is administered in combination with inhibitors of fructose-1,6-bisphosphatase (FBPase), such as, for example, CS-917 (MB-06322) or MB-07803 or those described in WO2006023515.

In one embodiment, the compound of the formula I is administered in combination with modulators of glucose transporter 4 (GLUT4), such as, for example, KST-48 (D.-O. Lee et al.: Arzneim.-Forsch. Drug Res. 54 (12), 835 (2004)).

In one embodiment, the compound of the formula I is administered in combination with inhibitors of glutamine-fructose-6-phosphate amidotransferase (GFAT), as are described for example in WO2004101528.

In one embodiment of the invention, the compound of the formula I is administered in combination with inhibitors of dipeptidylpeptidase IV (DPP-IV), such as, for example, vildagliptin (LAF-237), sitagliptin (MK-0431), saxagliptin ((BMS-477118), GSK-823093, PSN-9301, SYR-322, SYR-619, TA-6666, TS-021, GRC-8200, GW-825964X, KRP-104, DP-893 or as described in WO2003074500, WO2003106456, WO200450658, WO2005058901, WO2005012312, WO2005/012308, WO2006039325, WO2006058064, PCT/EP2005/007821, PCT/EP2005/008005, PCT/EP2005/008002, PCT/EP2005/008004, PCT/EP2005/008283, DE 10 2005 012874.2 or DE 10 2005 012873.4.

In one embodiment, the compound of the formula I is administered in combination with Januvia™, a fixed combination of sitagliptin phosphate with metformin hydrochloride.

In one embodiment, the compound of the formula I is administered in combination with inhibitors of 11-beta-hydroxysteroid dehydrogenase 1 (11β-HSD1), such as, for example, BVT-2733, JNJ-25918646, INCB-13739 or those as are described, for example, in WO200190090-94, WO200343999, WO2004112782, WO200344000, WO200344009, WO2004112779, WO2004113310, WO2004103980, WO2004112784, WO2003065983, WO2003104207, WO2003104208, WO2004106294, WO2004011410, WO2004033427, WO2004041264, WO2004037251, WO2004056744, WO2004058730, WO02004065351, WO2004089367, WO2004089380, WO2004089470-71, WO2004089896, WO2005016877, WO2005097759, WO2006010546, WO2006012227, WO2006012173, WO2006017542, WO2006034804, WO2006040329, WO2006051662, WO2006048750, WO2006049952, WO2006048331, WO2006050908, WO2006024627, WO2006040329, WO2006066109.

In one embodiment, the compound of the formula I is administered in combination with inhibitors of protein tyrosine phosphatase 1B (PTP1B), as are described for example in WO200119830-31, WO200117516, WO2004506446, WO2005012295, WO2005116003, PCT/EP2005/005311, PCT/EP2005/005321, PCT/EP2005/007151, PCT/EP2005/01294 or DE 10 2004 060542.4.

In one embodiment, the compound of the formula I is administered in combination with modulators of the sodium-dependent glucose transporter 1 or 2 (SGLT1, SGLT2) such as, for example, KGA-2727, T-1095, SGL-0010, AVE 2268 and SAR 7226 or as described, for example, in WO2004007517, WO200452903, WO200452902, PCT/EP2005/005959, WO2005085237, JP2004359630, WO2005121161, WO2006018150, WO2006035796, WO2006062224, WO2006058597 or by A. L. Handlon in Expert Opin. Ther. Patents (2005) 15(11), 1531-1540.

In one embodiment, the compound of the formula I is administered in combination with modulators of GPR40.

In one embodiment, the compound of the formula I is administered in combination with modulators of GPR119b as described, for example, in WO2004041274.

In one embodiment, the compound of the formula I is administered in combination with modulators of GPR119 as described, for example, in WO2005061489 (PSN-632408).

In one embodiment, the compound of the formula I is administered in combination with inhibitors of hormone-sensitive lipase (HSL) as described, for example, in WO2005073199.

In one embodiment, the compound of the formula I is administered in combination with inhibitors of acetyl-CoA carboxylase (ACC), such as, for example, those as described in WO199946262, WO200372197, WO2003072197, WO2005044814, WO2005108370, JP2006131559.

In one embodiment, the compound of the formula I is administered in combination with an inhibitor of phosphoenolpyruvate carboxykinase (PEPCK), such as, for example, those as described in WO2004074288.

In one embodiment, the compound of the formula I is administered in combination with an inhibitor of glycogen synthase kinase 3 beta (GSK-3 beta), as described, for example, in US2005222220, WO2005085230, PCT/EP2005/005346, WO2003078403, WO2004022544, WO2003106410, WO2005058908, US2005038023, WO2005009997, US2005026984, WO2005000836, WO2004106343, EP1460075, WO2004014910, WO2003076442, WO2005087727, WO2004046117.

In one embodiment, the compound of the formula I is administered in combination with an inhibitor of protein kinase C beta (PKC beta), such as, for example, ruboxistaurin.

In one embodiment, the compound of the formula I is administered in combination with an endothelin A receptor antagonist such as, for example, avosentan (SPP-301).

In one embodiment, the compound of the formula I is administered in combination with inhibitors of "I-kappaB kinase" (IKK inhibitors), as are described for example in WO2001000610, WO2001030774, WO2004022553 or WO2005097129.

In one embodiment, the compound of the formula I is administered in combination with modulators of the glucocorticoid receptor like those described, for example, in WO2005090336.

In a further embodiment, the compound of the formula I is administered in combination with CART modulators (see "Cocaine-amphetamine-regulated transcript influences energy metabolism, anxiety and gastric emptying in mice" Asakawa, A. et al.: Hormone and Metabolic Research (2001), 33(9), 554-558);

NPY antagonists (neuropeptide Y) such as, for example, naphthalene-1-sulfonic acid {4-[(4-aminoquinazolin-2-ylamino)methyl]cyclohexylmethyl}amide hydrochloride (CGP 71683A);

NPY-5 receptor antagonists such as L-152804 or S-2367 or as are described, for example in WO2006001318;

peptide YY 3-36 (PYY3-36) or analogous compounds, such as, for example, CJC-1682 (PYY3-36 conjugated with human serum albumin via Cys34), CJC-1643 (derivative of PYY3-36 which conjugates in vivo to serum albumin) or those as are described in WO2005080424;

CB1R (cannabinoid receptor 1) antagonists (such as, for example, rimonabant, SR147778, SLV-319, AVE-1625, MK-0364 or salts thereof or those compounds as described, for example, in EP 0656354, WO 00/15609, WO 02/076949, WO2005080345, WO2005080328, WO2005080343, WO2005075450, WO2005080357, WO200170700, WO2003026647-48, WO200302776, WO2003040107, WO2003007887, WO2003027069, U.S. Pat. No. 6,509,367, WO200132663, WO2003086288, WO2003087037, WO2004048317, WO2004058145, WO2003084930, WO2003084943, WO2004058744, WO2004013120, WO2004029204, WO2004035566, WO2004058249, WO2004058255, WO2004058727, WO2004069838, US20040214837, US20040214855, US20040214856, WO2004096209, WO2004096763, WO2004096794, WO2005000809, WO2004099157, US20040266845, WO2004110453, WO2004108728, WO2004000817, WO2005000820, US20050009870, WO200500974, WO2004111033-34, WO200411038-39, WO2005016286, WO2005007111, WO2005007628, US20050054679, WO2005027837, WO2005028456, WO2005063761-62, WO2005061509, WO2005077897, WO2006047516, WO2006060461, WO2006067428, WO2006067443, WO2006087480, WO2006087476, WO2006100208, WO2006106054, WO2006111849, WO2006113704, WO2007009705, WO2007017124, WO2007017126, WO2007018459, WO2007016460, WO02007020502, WO2007026215, WO2007028849, WO2007031720, WO2007031721, WO2007036945, WO2007038045, WO2007039740, US20070015810, WO2007046548, WO2007047737);

Cannabinoid receptor 1/cannabinoid receptor 2 (CB1/CB2)—modulating compounds as described, for example, in WO2007001939, WO2007044215, WO2007047737;

MC4 agonists (melanocortin-4 receptor agonists, for example 1-amino-1,2,3,4-tetrahydronaphthalene-2-carboxylic acid [2-(3a-benzyl-2-methyl-3-oxo-2,3,3a,4,6,7-hexahydropyrazolo[4,3-c]pyridin-5-yl)-1-(4-chlorophenyl)-2-oxoethyl]amide; (WO 01/91752)) or LB53280, LB53279, LB53278 or THIQ, MB243, RY764, CHIR-785, PT-141 or those that are described in WO2005060985, WO2005009950, WO2004087159, WO2004078717, WO2004078716, WO2004024720, US20050124652, WO2005051391, WO2004112793, WOUS20050222014, US20050176728, US20050164914, US20050124636, US20050130988, US20040167201, WO2004005324, WO2004037797, WO2005042516, WO2005040109, WO2005030797, US20040224901, WO200501921, WO200509184, WO2005000339, EP1460069, WO2005047253, WO2005047251, EP1538159, WO2004072076, WO2004072077, WO2006021655-57;

orexin receptor antagonists (for example 1-(2-methylbenzoxazol-6-yl)-3-[1,5]naphthyridin-4-ylurea hydrochloride (SB-334867-A) or those as are described for example in WO200196302, WO200185693, WO2004085403, WO2005075458, WO2006/67224);

histamine H3 receptor agonists (for example 3-cyclohexyl-1-(4,4-dimethyl-1,4,6,7-tetrahydroimidazo[4,5-c]pyridin-5-yl)propan-1-one oxalic acid salt (WO 00/63208) or those as are described in WO200064884, WO2005082893);

CRF antagonists (corticotropin-releasing factor antagonists, for example [2-methyl-9-(2,4,6-trimethylphenyl)-9H-1,3,9-triazafluoren-4-yl]dipropylamine (WO 00/66585));

CRF BP antagonists (for example urocortin);

urocortin agonists;

agonists of the beta-3 adrenoreceptor such as, for example, 1-(4-chloro-3-methanesulfonylmethylphenyl)-2-[2-(2,3-dimethyl-1H-indol-6-yloxy)ethylamino]ethanol hydrochloride (WO 01/83451) or solabegron (GW-427353) or N-5984 (KRP-204), or those as are described in JP2006111553;

MSH (melanocyte-stimulating hormone) agonists;

MCH (melanin-concentrating hormone) receptor antagonists (such as, for example, NBI-845, A-761, A-665798, A-798, ATC-0175, T-226296, T-71, GW-803430 or compounds such as are described in WO2003/15769, WO2005085200, WO2005019240, WO2004011438, WO2004012648, WO2003015769, WO2004072025, WO2005070898, WO2005070925, WO2004039780, WO2003033476, WO2002006245, WO2002089729, WO2002002744, WO2003004027, FR2868780, WO2006010446, WO2006038680, WO2006044293, WO2006044174);

CCK-A agonists (cyclic pseudopeptide cholecystokinin-A agonists such as, for example, {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525) or SR-146131 (WO 0244150) or SSR-125180) or those as are described in WO2005116034;

serotonin reuptake inhibitors (e.g. dexfenfluramine);

mixed serotoninergic and noradrenergic compounds (for example WO 00/71549);

5-HT receptor agonists, for example 1-(3-ethylbenzofuran-7-yl)piperazine oxalic acid salt (WO 01/09111);

5-HT2C receptor agonists (such as, for example, lorcaserin hydrochloride (APD-356) or BVT-933 or those as are described in WO200077010, WO20077001-02, WO2005019180, WO2003064423, WO200242304, WO2005082859);

5-HT6 receptor antagonists as described, for example, in WO2005058858;

bombesin receptor agonists (BRS-3 agonists);

galanin receptor antagonists;

growth hormone (e.g. human growth hormone or AOD-9604);

growth hormone-releasing compounds (tertiary butyl 6-benzyloxy-1-(2-diisopropyl-aminoethylcarbamoyl)-3,4-dihydro-1H-isoquinoline-2-carboxylate (WO 01/85695));

growth hormone secretagogue receptor antagonists (ghrelin antagonists) such as, for example, A-778193 or those as are described in WO2005030734;

TRH agonists (thyrotrophin-releasing hormone—see, for example, EP 0 462 884);

uncoupling protein 2 or 3 modulators;

leptin agonists (see, for example, Lee, Daniel W.; Leinung, Matthew C.; Rozhayskaya-Arena, Marina; Grasso, Patricia. Leptin agonists as a potential approach to the treatment of obesity. Drugs of the Future (2001), 26(9), 873-881);

DA agonists (dopamine agonist, for example, bromocriptine or Doprexin);

lipase/amylase inhibitors (for example WO 00/40569);

inhibitors of diacylglycerol O-acyltransferases (DGATs) such as for example BAY-74-4113 or as described for example in US2004/0224997, WO2004094618, WO200058491, WO2005044250, WO2005072740, JP2005206492, WO2005013907, WO2006004200, WO2006019020, WO2006064189;

inhibitors of fatty acid synthase (FAS) such as, for example, C75 or those as described in WO2004005277;

oxyntomodulin;

oleoyl-estrone or thyroid hormone receptor agonists such as, for example: KB-2115 or those as described in WO20058279, WO200172692, WO200194293, WO2003084915, WO2004018421, WO2005092316.

In one embodiment, the further active ingredient is varenicline tartrate, a partial agonist of the alpha 4-beta 2 nicotinic acetylcholine receptor.

In one embodiment, the further active ingredient is trodusquemine.

In one embodiment, the further active ingredient is a modulator of the SIRT1 enzyme, a member of the human sirtuin enzyme family.

In one embodiment of the invention, the further active ingredient is leptin; see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In one embodiment, the further active ingredient is dexamphetamine or amphetamine.

In one embodiment, the further active ingredient is fenfluramine or dexfenfluramine.

In another embodiment, the further active ingredient is sibutramine.

In one embodiment, the further active ingredient is mazindole or phentermine.

In one embodiment, the further active ingredient is a diphenylazetidinone derivative, as described, for example, in U.S. Pat. No. 6,992,067 or U.S. Pat. No. 7,205,290.

In one embodiment, the compound of the formula I is administered in combination with bulking agents, preferably insoluble bulking agents (see, for example, Carob/CAROMAX® (Zunft H J; et al., Carob pulp preparation for treatment of hypercholesterolemia, ADVANCES IN THERAPY (2001 September-October), 18(5), 230-6. Caromax is a carob-containing product from Nutrinova, Nutrition Specialties & Food Ingredients GmbH, Industriepark Höchst, 65926 Frankfurt/Main). Combination with CAROMAX® is possible in one preparation or by separate administration of compounds of the formula I and CAROMAX®. CAROMAX® can in this connection also be administered in the form of food products such as, for example, in bakery products or muesli bars.

It will be understood that every suitable combination of the compounds of the invention with one or more of the aforementioned compounds and optionally one or more further pharmacologically active substances will be regarded as falling within the protection conferred by the present invention.

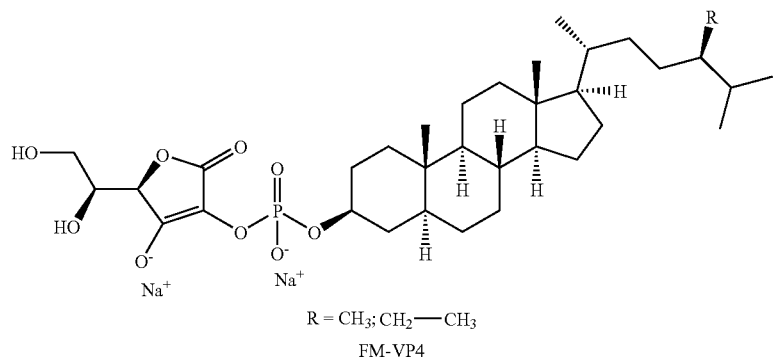
R = CH₃; CH₂—CH₃
FM-VP4
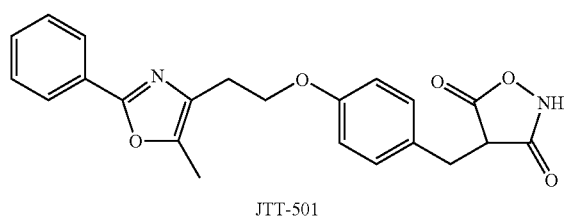
JTT-501
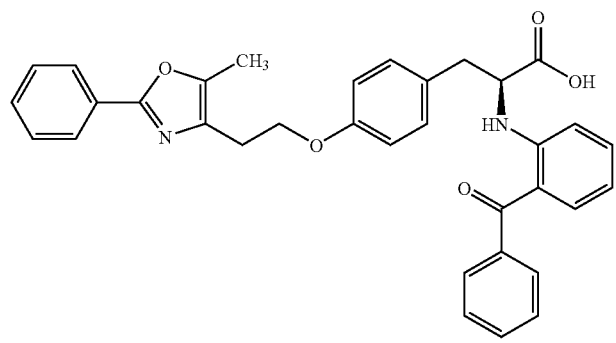
GI 262570
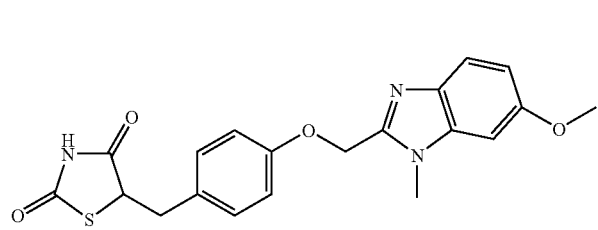
CS-011
rivoglitazone
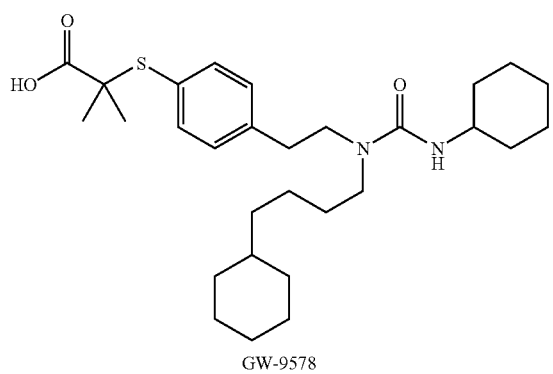
GW-9578
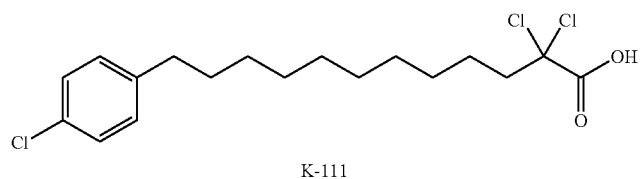
K-111
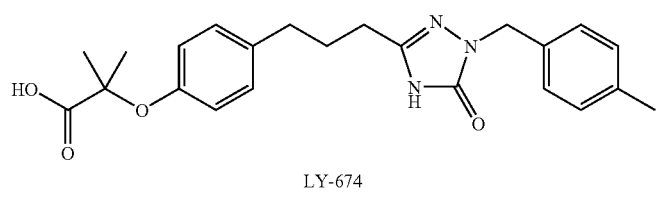
LY-674

-continued
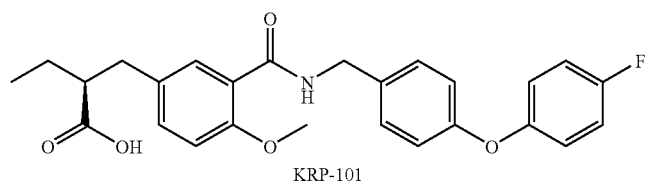
KRP-101
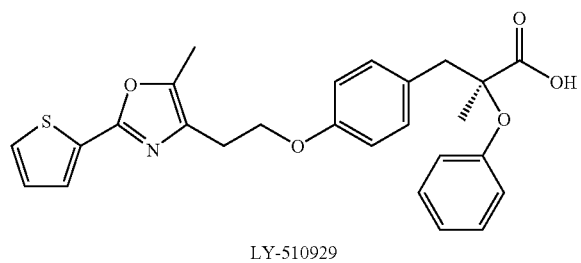
LY-510929
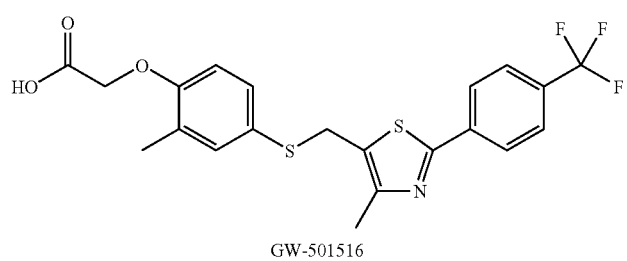
GW-501516
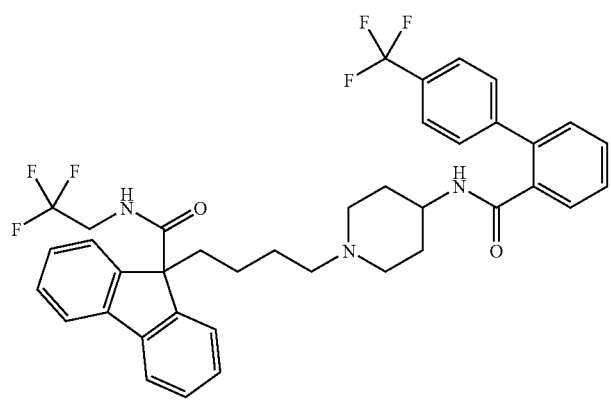
BMS-201038
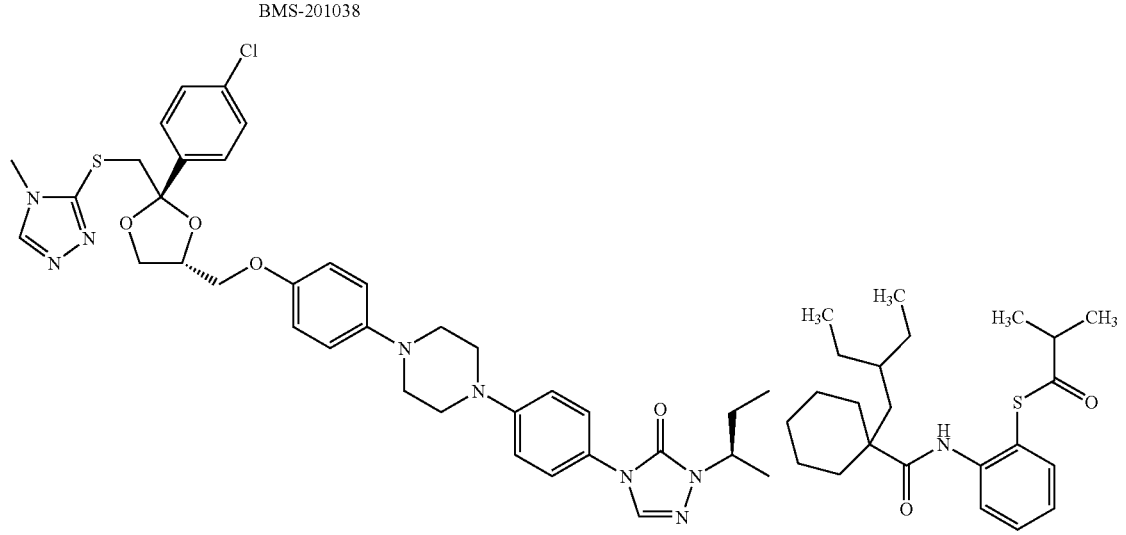
R-103757       JTT-705

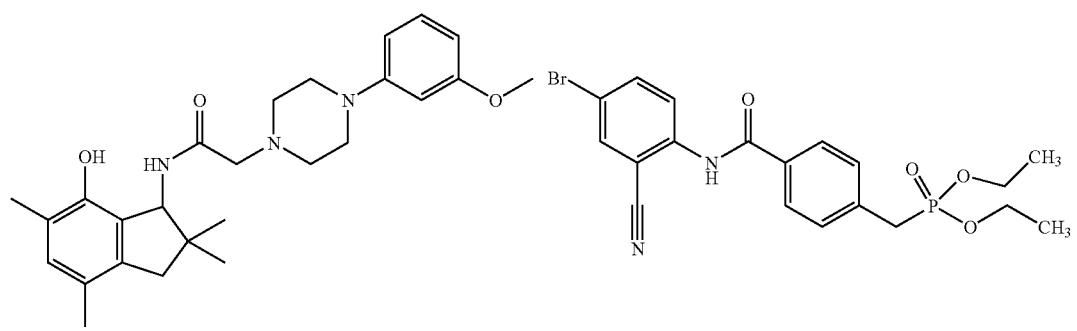
OPC-14117
NO-1886
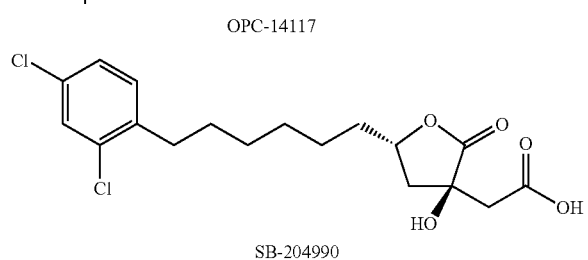
SB-204990
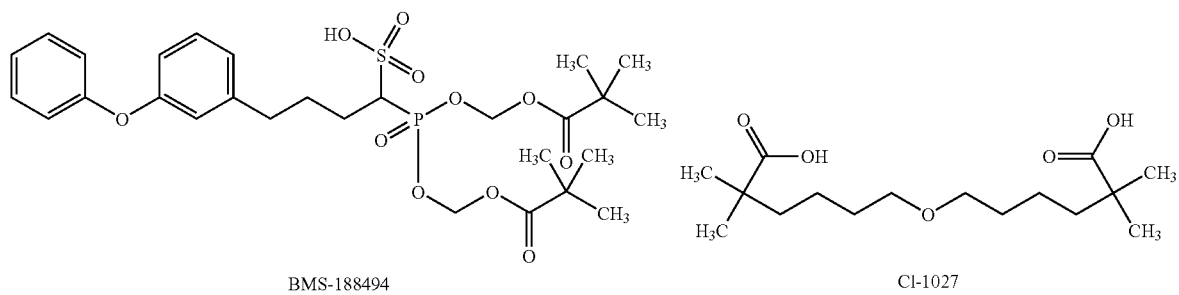
BMS-188494
Cl-1027
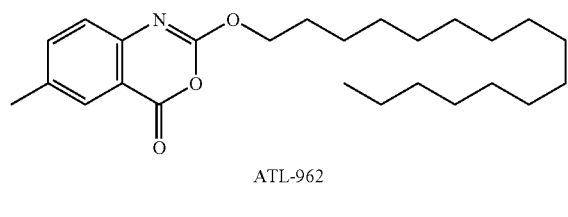
ATL-962
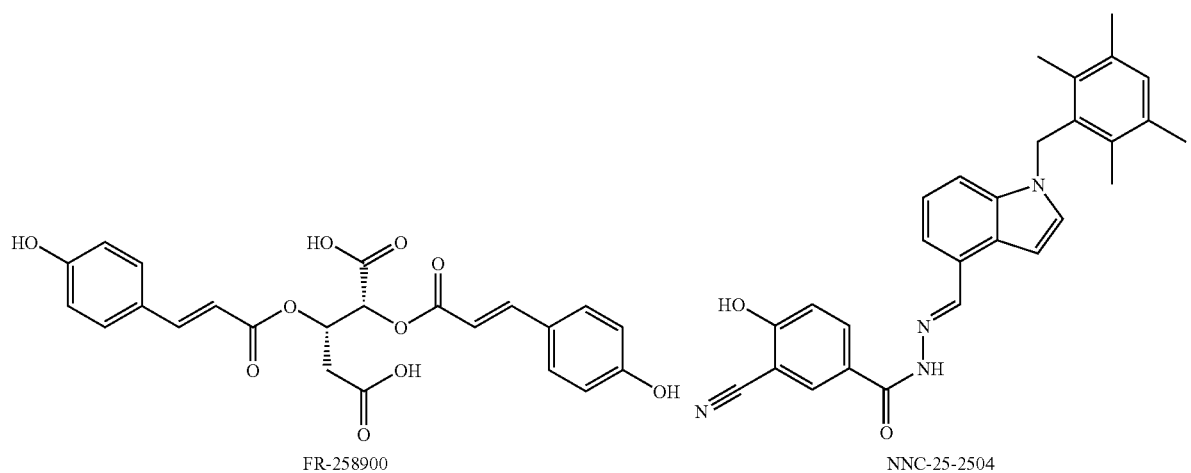
FR-258900
NNC-25-2504

-continued
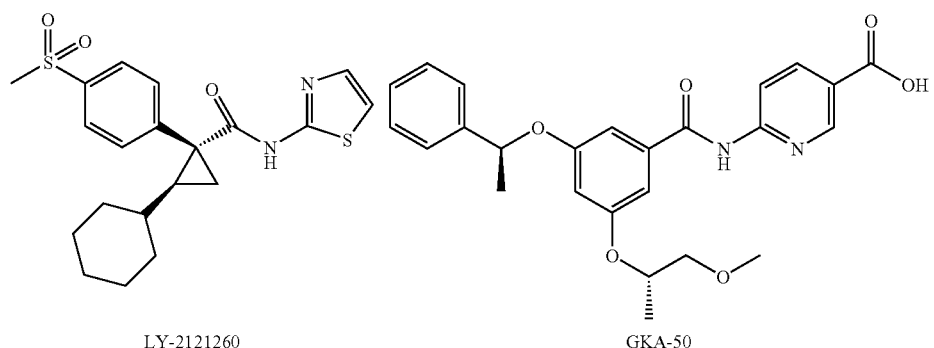
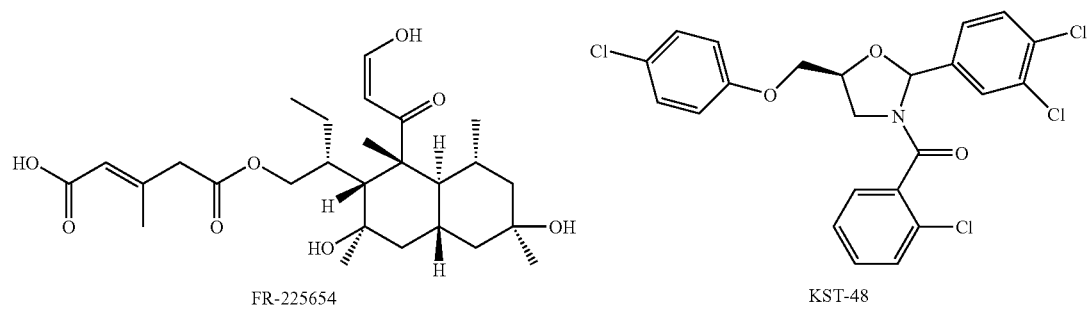
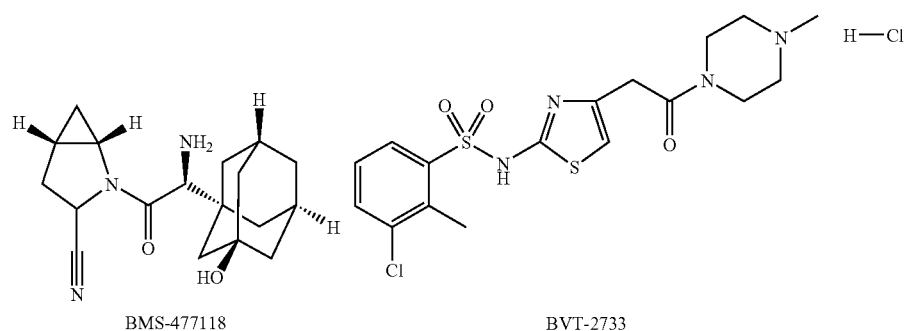
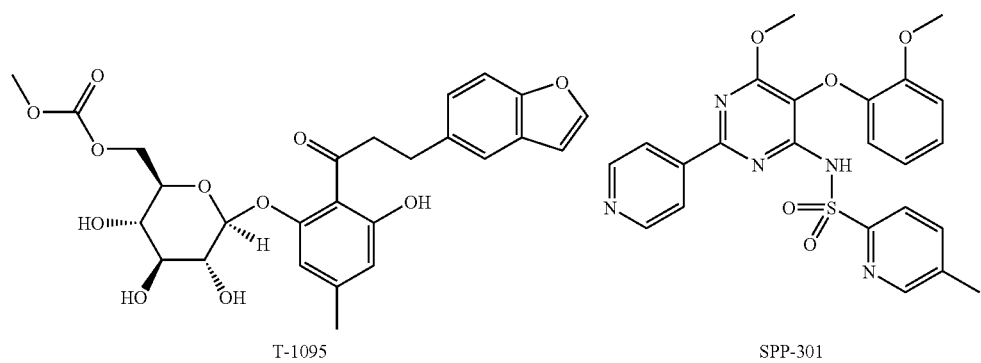

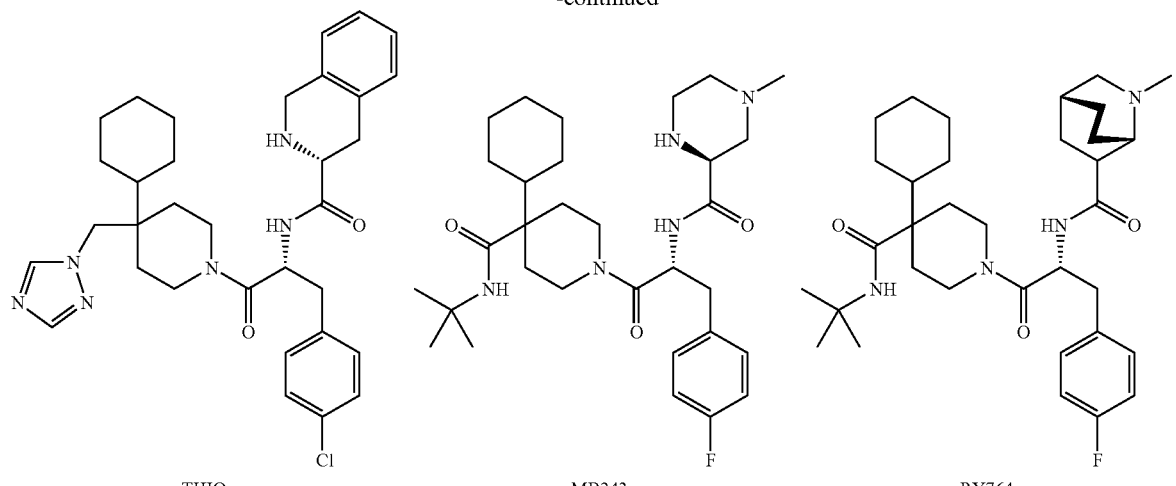
THIQ
MB243
RY764
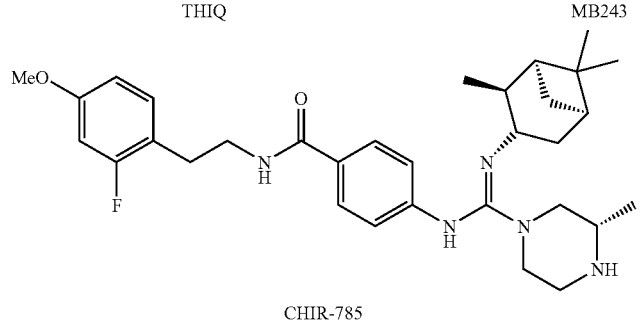
CHIR-785
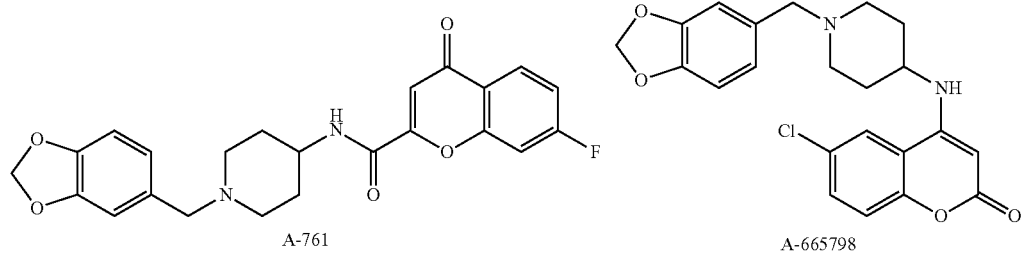
A-761
A-665798
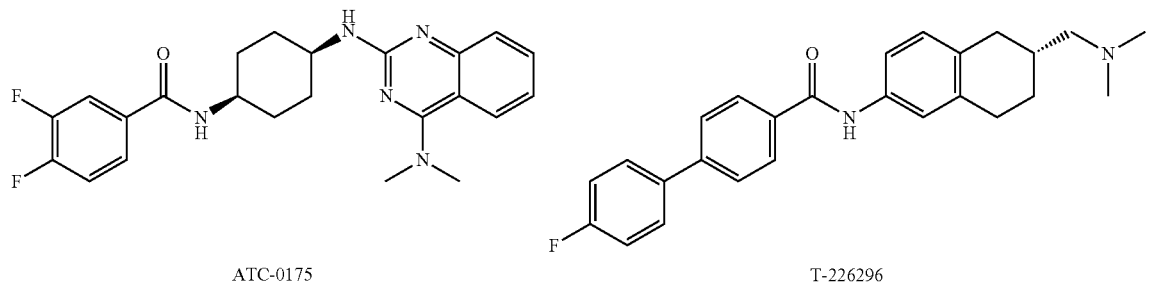
ATC-0175
T-226296
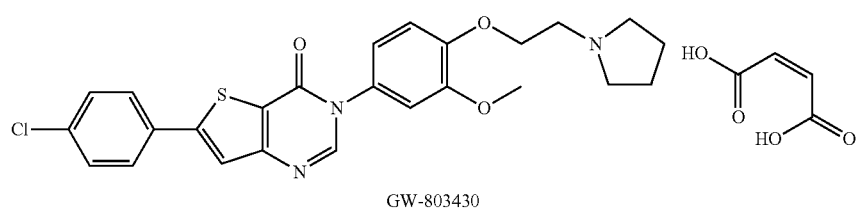
GW-803430

-continued
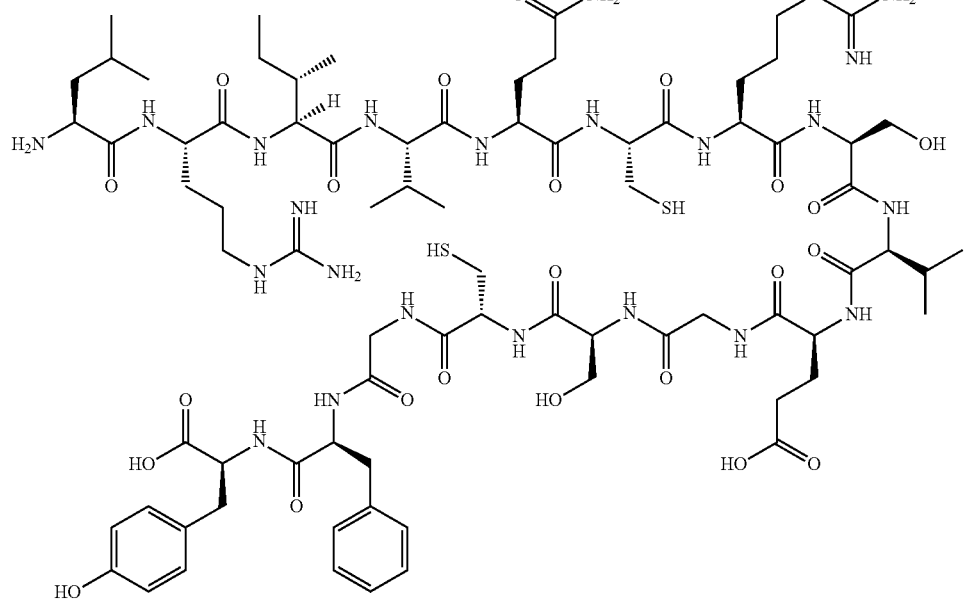
AOD-9604
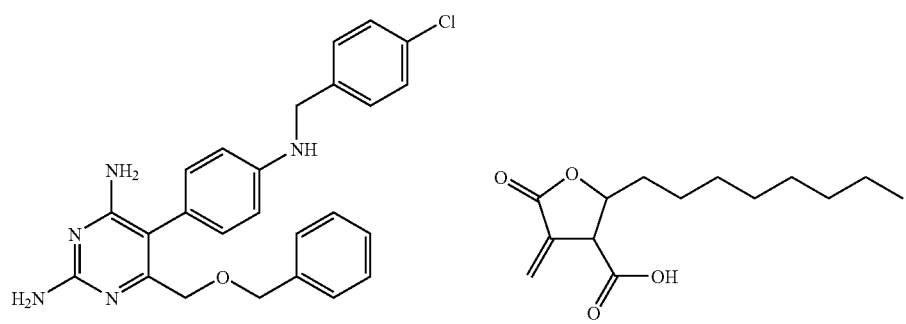
A-778193      C75
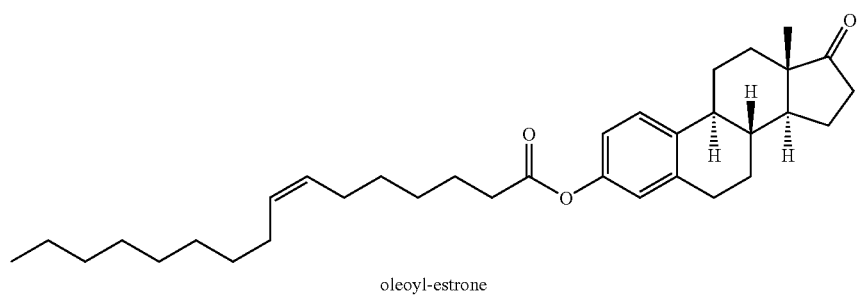
oleoyl-estrone
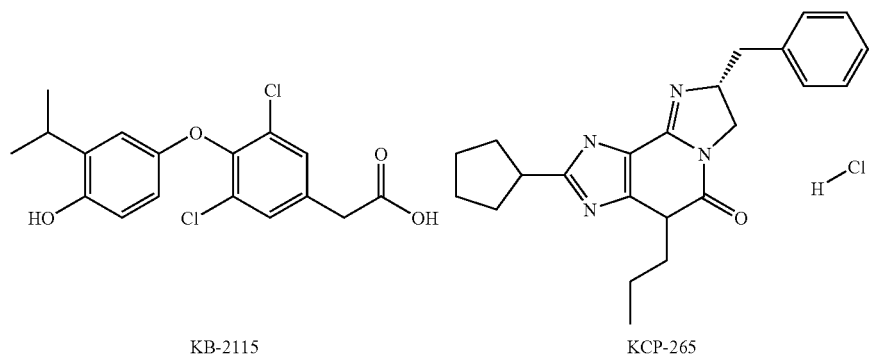
KB-2115      KCP-265

-continued
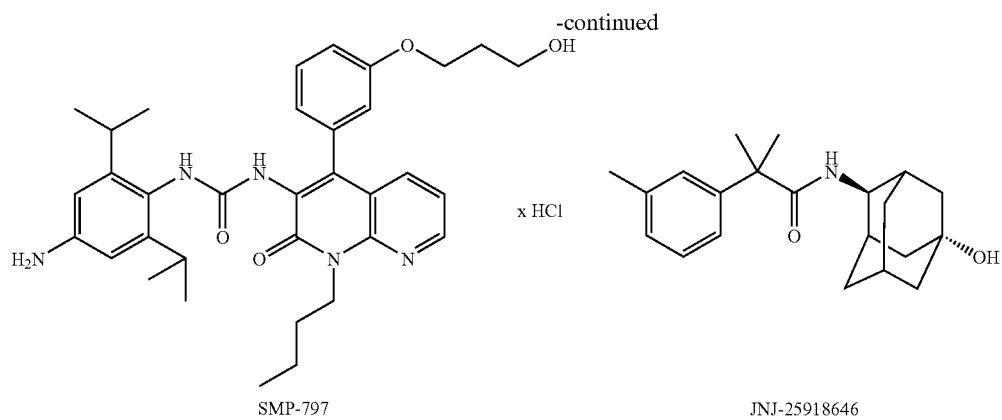
SMP-797    JNJ-25918646
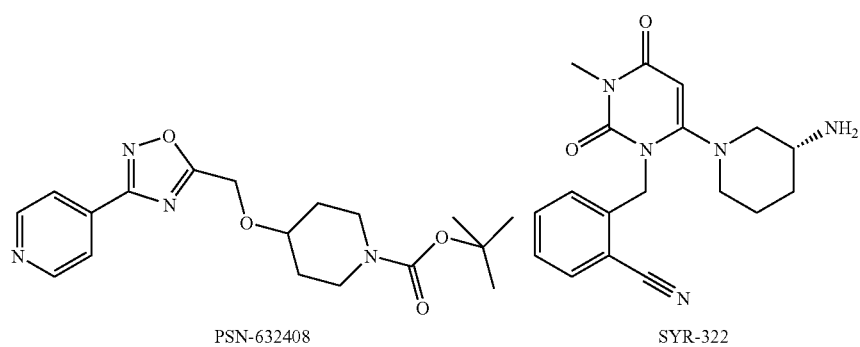
PSN-632408    SYR-322
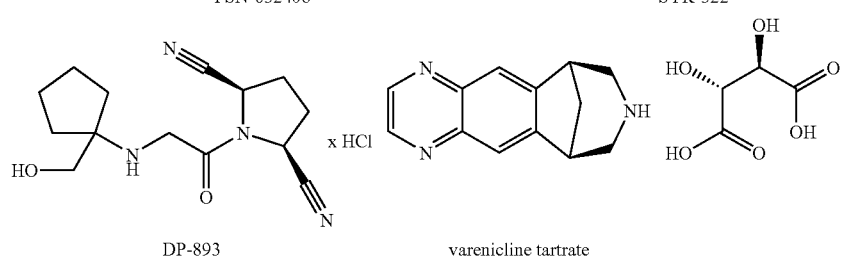
DP-893    varenicline tartrate
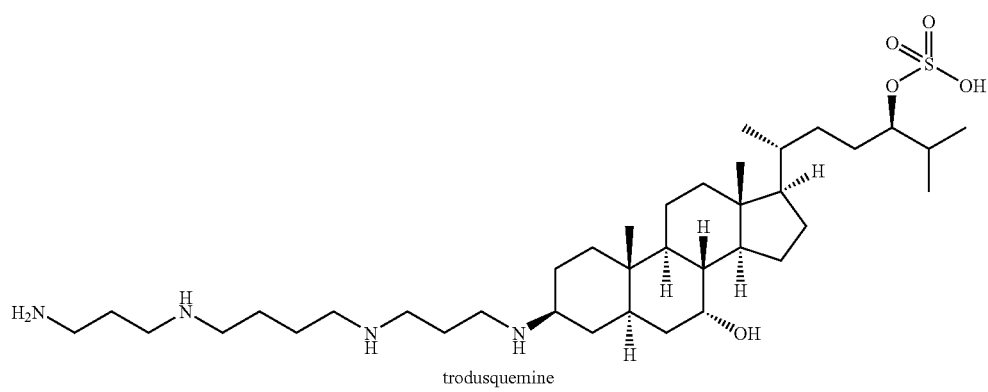
trodusquemine
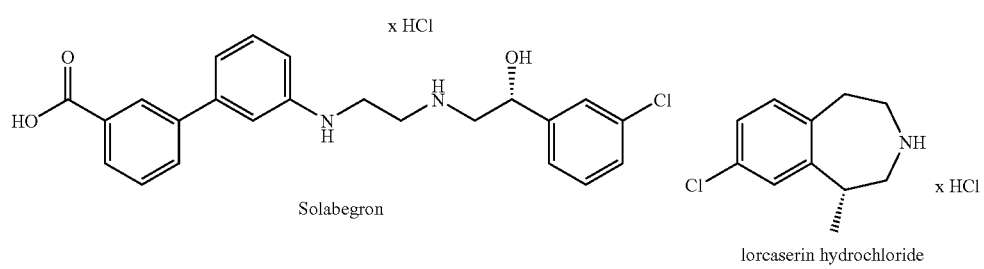
Solabegron    lorcaserin hydrochloride

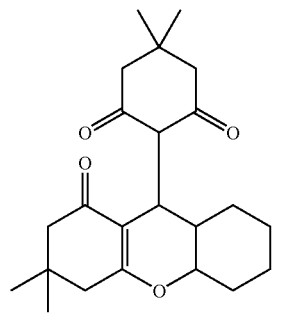
L-152084
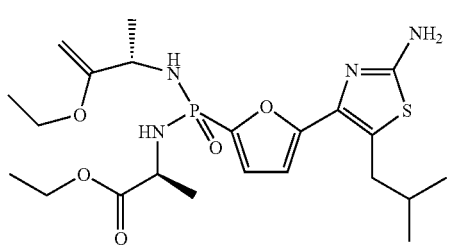
MB-06322
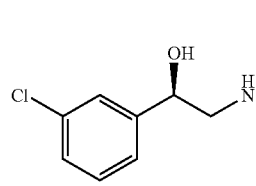
N-5984
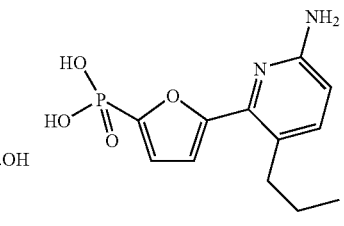
MB-07803
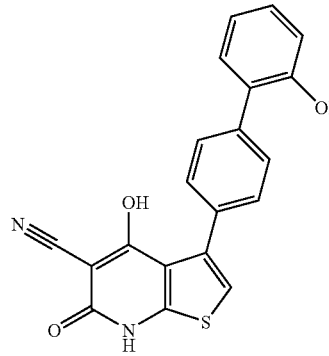
A-769662
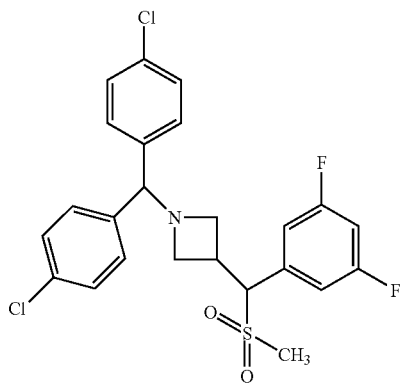
AVE1625
The examples given below serve to illustrate the invention, but without limiting it.
TABLE 1
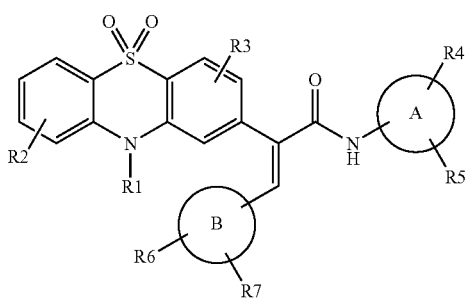
| Example | R1 | R2 | R3 | A | R4 | R5 | B | R6 | R7 |
|---|---|---|---|---|---|---|---|---|---|
| 1 | CH₃ | H | H | pyrazole | 1-CH₃ | H | cyclopentyl | H | H |

TABLE 1-continued

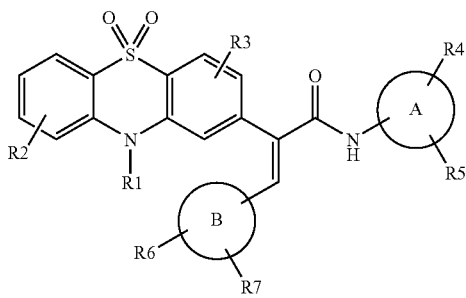

| Example | R1 | R2 | R3 | A | R4 | R5 | B | R6 | R7 |
|---------|-----|----|----|---|------|----|---|-------|----|
| 2 | CH₃ | H | H | pyrazole | 1-CH₂Ph | H | cyclopentyl | H | H |
| 3 | H | H | H | pyrazole | 1-CH₃ | H | cyclohexyl | 4-'=O' | H |
| 4 | H | H | H | thiazolo-pyridine | 5-OCH₃ | H | cyclohexyl | 4-'=O' | H |
| 5 | H | H | H | pyrazole | 1-CH₃ | H | cyclohexyl | 4-'=O' | H |

The broken line in the radicals A and B indicates the point of attachment of the bond to the ring.

The activity of the compounds was tested as follows:
Enzymatic Test of Glucokinase Activators
Human Glucokinase Human glucokinase is expressed as a fusion protein with glutathione S-transferase (GST) in *E. coli* Bl21 and purified by affinity chromatography. GSH is cleaved off by digestion with factor Xa, and the glucokinase polypeptide beginning with Ser-6 is obtained. The latter is purified chromatographically. At room temperature, a typical glucokinase preparation has a specific activity of 30 U/mg protein.

Enyzymatic Test

The activity of glucokinase and the effect of compounds on this activity are determined by a coupled optical test at 25° C. The test volume is 100 µl. The test composition is: 25 mM HEPES/NaOH (Merck; #110110) pH 7, 25 mM KCl (Merck; #04933), 2 mM MgCl₂ (Merck; #05833), 1 mM dithiothreitol (Merck; #112013), 1 mM NAD (Sigma; #N1511), 5 mM glucose (Merck; #108337), 1 mM ATP (Sigma; #A2383), 0.1% (w/v) bovine serum albumin (Merck; #112018), 0.002 U glucokinase preparation and 3.2 U glucose 6-phosphate dehydrogenase (Sigma; #G8529). The mixture furthermore contains a test compound. The test compounds are in each case dissolved in 10 mM DMSO and are tested at final concentrations of 0 µM, 0.1 µM, 0.3 µM, 1 µM, 3 µM, 10 µM, 30 µM and 100 µM. The final concentration of DMSO in the test is 1% (v/v). The reaction is started by addition of ATP. The absorption of the mixture at 340 nm is determined immediately after the addition of ATP and then 25 min later using a multiwell plate photometer (from Labsystems, Multiskan Ascent). The change of the absorption during this period is calculated.

Evaluation:

The crude data of the changes in extinction are transferred into a Microsoft Excel file. The value for 0 µM test compound is assigned to be 100%. Dose/activity curves are calculated using the program XL.Fit according to the instructions of the manufacturer (IDBS). The concentration of a test compound which increases the enzymatic activity by 50% is defined as $EC_{150}$. The maximum fold stimulation corresponds to the ratio of the highest change in extinction in the concentration range of a test compound to the change of the absorption without test substance.

TABLE 2

Biological activity

| Example No | $EC_{150}$ [µM] | Fold induction |
|------------|-----------------|----------------|
| 1 | 1.70 | 3.2 |
| 4 | 0.2 | 4.8 |

It is evident from the measured data in the table that the compounds according to the invention activate glucokinase. These compounds are therefore suitable in particular for lowering the blood glucose level and for the treatment of diabetes.

Process

The compounds of the formula I according to the invention can be prepared according to the reaction scheme below:

Process A:

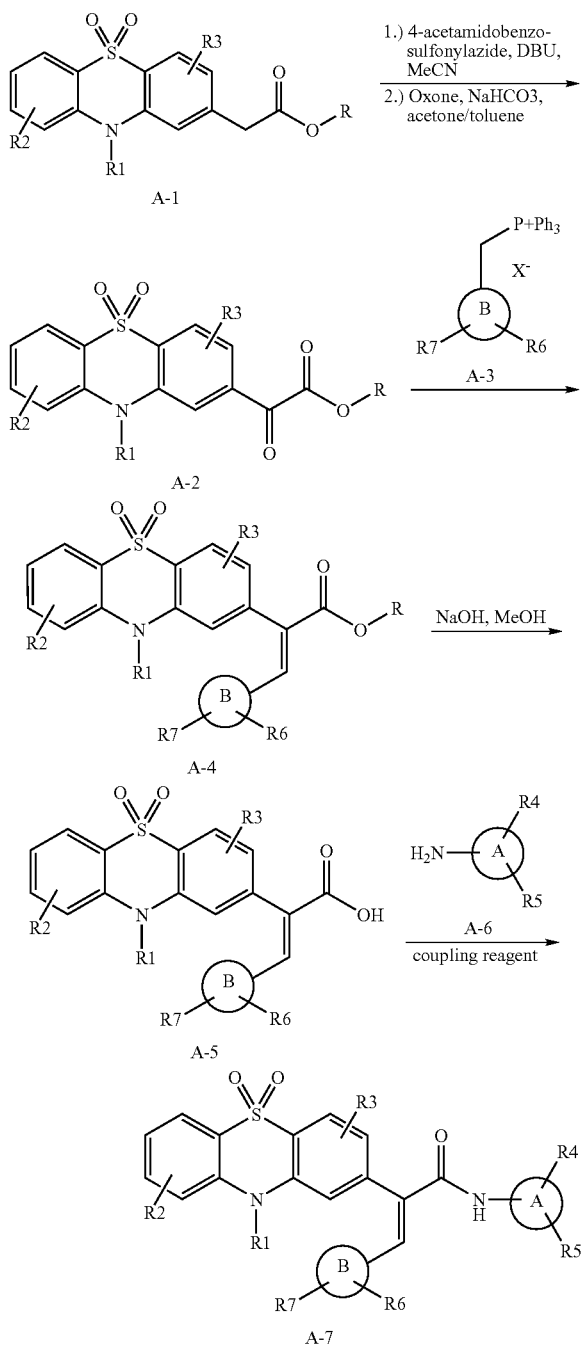

The phenothiazine ester (R=methyl or ethyl) of the general formula A-1 (preparation described in DE2007-002) where R1, R2 and R3 have the meanings given above is, in a polar aprotic solvent, such as, for example, acetonitrile, deprotonated with a base, such as, for example, 1,8-diazabicyclo[5.4.0]undec-7-ene at room temperature and then, at low temperature (−20° C.-0° C.), admixed with 4-acetaminobenzenesulfonyl azide and then allowed to react at room temperature. The diazo compound formed is not isolated but immediately, by addition of an oxidizing agent, such as, for example, Oxone, in a solvent mixture, such as, for example, acetone/toluene, in the presence of a base, such as, for example, sodium bicarbonate, converted into the keto compound of the general formula A-2. The keto compound of the general formula A-2 is converted with a Wittig reagent which is obtained by releasing the corresponding Wittig salt of the general formula A-3 using a base, such as, for example, lithium hexamethyldisilazide, in a polar aprotic solvent, such as tetrahydrofuran, into the α,β-unsaturated ester of the general formula A-4.

The ester group of the compound of the general formula A-4 is hydrolyzed with a base such as, for example, aqueous sodium hydroxide solution in a polar protic solvent mixture such as methanol/water to give the carboxylic acid of the general formula A-5. Under the action of a coupling agent such as, for example, O-[cyano(ethoxycarbonyl)methylenamino]-1,1,3,3-tetramethyluronium tetrafluoroborate (TOTU) or [dimethylamino-([1,2,3]triazolo[4,5-b]pyridin-3-yloxy)methylene]dimethylammonium hexafluorophosphate (HATU)/[1,2,3]triazolo[4,5-b]pyridin-3-ol (HOAT) in the presence of a base such as, for example, diisopropylethylamine in a polar aprotic solvent such as N,N-dimethylformamide, the carboxylic acid of the general formula A-5 is reacted with the amine of the general formula A-6 in which A, R4 and R5 have the meanings described above, to give the amide of the general formula A-7. The racemic compounds of the general formula A-7 can be separated into the enantiomers by chromatography on a chiral phase.

Examples 1-5 were prepared according to process A.

The abbreviations used denote:

| | |
|---|---|
| Ac | acetyl |
| Bn | benzyl |
| BOC | tert-butyloxycarbonyl |
| iBu | isobutyl |
| tBu | tert-butyl |
| BuLi | n-butyllithium |
| TLC | thin-layer chromatography |
| DCI | direct chemical ionization (in MS) |
| DCM | dichloromethane |
| DMAP | 4-N,N-dimethylaminopyridine |
| DMF | N,N-dimethylformamide |
| DMSO | dimethyl sulfoxide |
| EA | ethyl acetate |
| ent | enantiomer/enantiomerically pure |
| EI | electron impact ionization (in MS) |
| eq | equivalent |
| ESI | electron spray ionization (in MS) |
| Et | ethyl |
| GC | gas chromatography |
| HATU | [dimethylamino([1,2,3]triazolo[4,5-b]pyridin-3-yloxy)-methylene]dimethylammonium hexafluorophosphate |
| HOAT | [1,2,3]triazolo[4,5-b]pyridin-3-ol |
| HPLC | high pressure, high performance liquid chromatography |
| LiHMDS | Lithium hexamethyldisilazide |
| LC-MS | liquid chromatography-coupled mass spectroscopy |
| m | meta |
| M | molar |
| mCPBA | meta-chloroperbenzoic acid |
| Me | methyl |
| MeCN | acetonitrile |
| MS | mass spectroscopy |
| NMR | nuclear magnetic resonance spectroscopy |
| o | ortho |
| oxone | potassium monopersulfate sulfate |
| p | para |

Exemplary Syntheses According to Process A

EXAMPLE 1

(E)-3-cyclopentyl-2-(10-methyl-5,5-dioxo-5,10-dihydrophenothiazin-2-yl)-N-(1-methyl-1H-pyrazol-3-yl)acrylamide

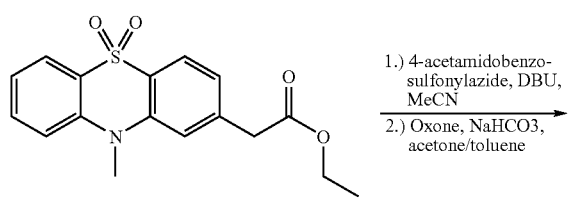

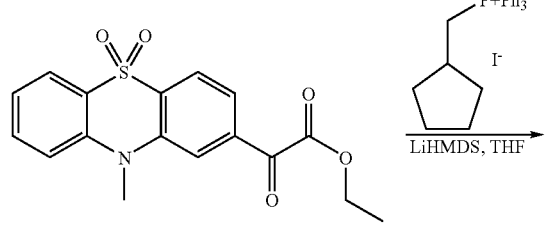

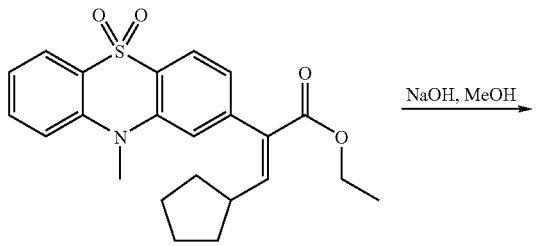

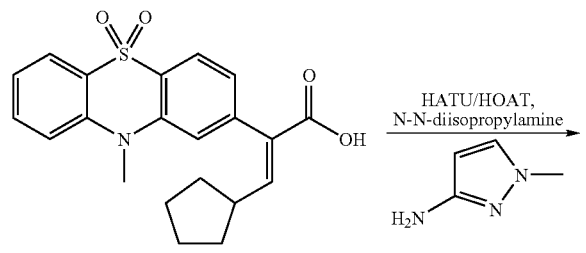

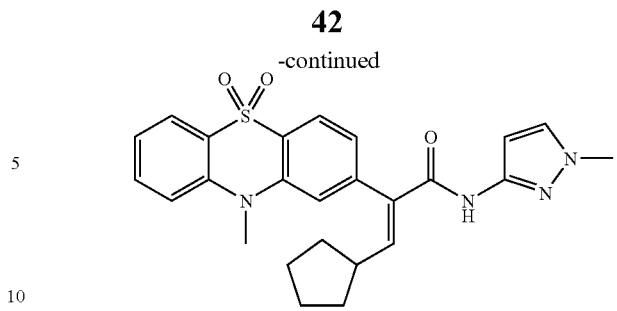

ethyl(10-methyl-5,5-dioxo-5,10-dihydrophenothiazin-2-yl)oxo acetate

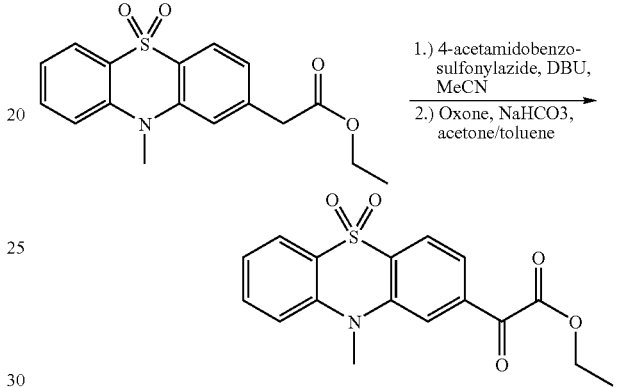

2.24 g ethyl(10-methyl-5,5-dioxo-5,10-dihydrophenothiazin-2-yl)acetate are dissolved in 50 ml of acetonitrile, and 0.71 ml of DBU is added. After 15 minutes of stirring at room temperature, 1.95 g of 4-acetaminobenzenesulfonyl azide are added with ice-cooling. The reaction mixture is stirred at room temperature for twelve hours. (Rf of the diazo compound in n-heptane:ethyl acetate=2:1 Rf=0.15). 50 mol of toluene, 35 ml of acetone and 50 ml of water are added to the reaction mixture, followed by 40.3 g of Oxone and 21.78 g of NaHCO$_3$. The mixture is stirred at room temperature for one hour. The reaction mixture is diluted by addition of 200 ml of water and extracted three times with in each case 300 ml of ethyl acetate. The combined organic phases are dried over MgSO$_4$ and then concentrated under reduced pressure. The residue obtained in this manner is purified on silica gel using the mobile phase 100% n-heptane=>100% ethyl acetate as a linear gradient. This gives 1.87 g of ethyl(10-methyl-5,5-dioxo-5,10-dihydrophenothiazin-2-yl)oxo acetate. C17H15NO5S (345.38), LCMS(ESI): 346.1 (M+H$^+$), Rf(n-heptane:ethyl acetate=2:1)=0.11.

Ethyl(E)-3-cyclopentyl-2-(10-methyl-5,5-dioxo-5,10-dihydrophenothiazin-2-yl)acrylate

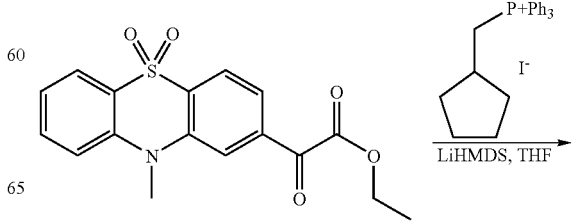

| Pd/C | palladium on carbon |
| Ph | phenyl |
| iPr | isopropyl |
| nPr | n-propyl |
| rac | racemic/racemic mixture |
| Rf | retention time (in TLC) |
| RP | reversed phase |
| tert | tertiary |
| THF | tetrahydrofuran |
| TOTU | O-[cyano(ethoxycarbonyl)methylenamino]-1,1,3,3-tetramethyluronium tetrafluoroborate |

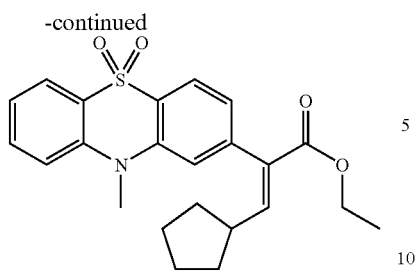

Under argon, 1.47 ml of 1,1,1,3,3,3-hexamethyldisilazane are dissolved in 20 ml of tetrahydrofuran. 2.57 ml of n-butyllithium (2.5 M in n-hexane) are added dropwise with ice-cooling, and the mixture is stirred at 0° C. for 30 minutes. With ice-cooling, this solution is then added dropwise to a stirred suspension of 2.53 g of cyclopentylmethyltriphenylphosphonium iodide in 60 ml of tetrahydrofuran. The reaction mixture is stirred at 0° C. for 45 minutes, 1.85 g of ethyl(10-methyl-5,5-dioxo-5,10-dihydrophenothiazine-2-yl)oxo acetate, dissolved in 20 ml of THF, are then added dropwise and the mixture is stirred at 0° C. for one hour. The cooling bath is removed and the mixture is slowly warmed to room temperature. The reaction mixture is stirred at room temperature overnight. 30 ml of saturated sodium chloride solution are then added, and the mixture is extracted three times with in each case 100 ml of ethyl acetate. The combined organic phases are dried over MgSO$_4$ and then concentrated under reduced pressure. The residue is purified on silica gel using the mobile phase n-heptane:ethyl acetate (100%:0%) =>n-heptane:ethyl acetate (40%:60%). This gives 1.58 g of ethyl(E)-3-cyclopentyl-2-(10-methyl-5,5-dioxo-5,10-dihydrophenothiazine-2-yl)acrylate as a colorless solid.

C23H25NO4S (411.52), LCMS(ESI): 412.2 (M+H$^+$), Rf(n-heptane:ethyl acetate=2:1)=0.27.

(E)-3-cyclopentyl-2-(10-methyl-5,5-dioxo-5,10-dihydrophenothiazine-2-yl)acrylic acid 1.58 g of ethyl(E)-3-cyclopentyl-2-(10-methyl-5,5-dioxo-5,10-dihydrophenothiazin-2-yl)acrylate are dissolved in 130 ml of methanol, and 13.44 ml of 2 M NaOH solution are added. The reaction mixture is heated at the boil under reflux for two hours. The methanol is removed under reduced pressure, and the reaction mixture is adjusted to pH 4 by addition of 2N hydrochloric acid. The precipitated solid is filtered off with suction and dried under high vacuum. This gives 1.46 g of (E)-3-cyclopentyl-2-(10-methyl-5,5-dioxo-5,10-dihydrophenothiazin-2-yl)acrylic acid.

C21H21NO4S (383.47), LCMS(ESI): 384.1 (M+H$^+$).

(E)-3-cyclopentyl-2-(10-methyl-5,5-dioxo-5,10-dihydrophenothiazin-2-yl)-N-(1-methyl-1H-pyrazol-3-yl)acrylamide

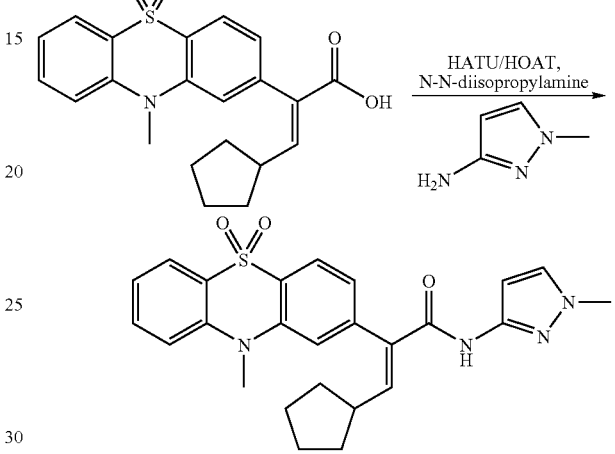

480 mg of (E)-3-cyclopentyl-2-(10-methyl-5,5-dioxo-5,10-dihydrophenothiazin-2-yl)acrylic acid, 122 mg of commercial 1-methyl-1H-pyrazol-3-ylamine and 0.76 ml of N,N-diisopropylethylamine are dissolved in 7 ml of dimethylformamide. 571 mg of HATU and 204 mg of HOAT are added, and the mixture is stirred at room temperature for one hour. The reaction mixture is then diluted by addition of 100 ml of ethyl acetate and washed five times with in each case 30 ml of water. The organic phase is dried over MgSO$_4$, and the solvent is then removed under reduced pressure. The residue is purified on silica gel using the mobile phase n-heptane (100%)=>:ethyl acetate (100%). This gives 360 mg of (E)-3-cyclopentyl-2-(10-methyl-5,5-dioxo-5,10-dihydrophenothiazin-2-yl)-N-(1-methyl-1H-pyrazol-3-yl)acrylamide.

C25H26N4O3S (462.57), LCMS(ESI): 463.2 (M+M$^+$), Rf(ethyl acetate)=0.37.

EXAMPLE 2

(E)-N-(1-benzyl-1H-pyrazol-3-yl)-3-cyclopentyl-2-(10-methyl-5,5-dioxo-5,10-dihydro-phenothiazin-2-yl)acrylamide

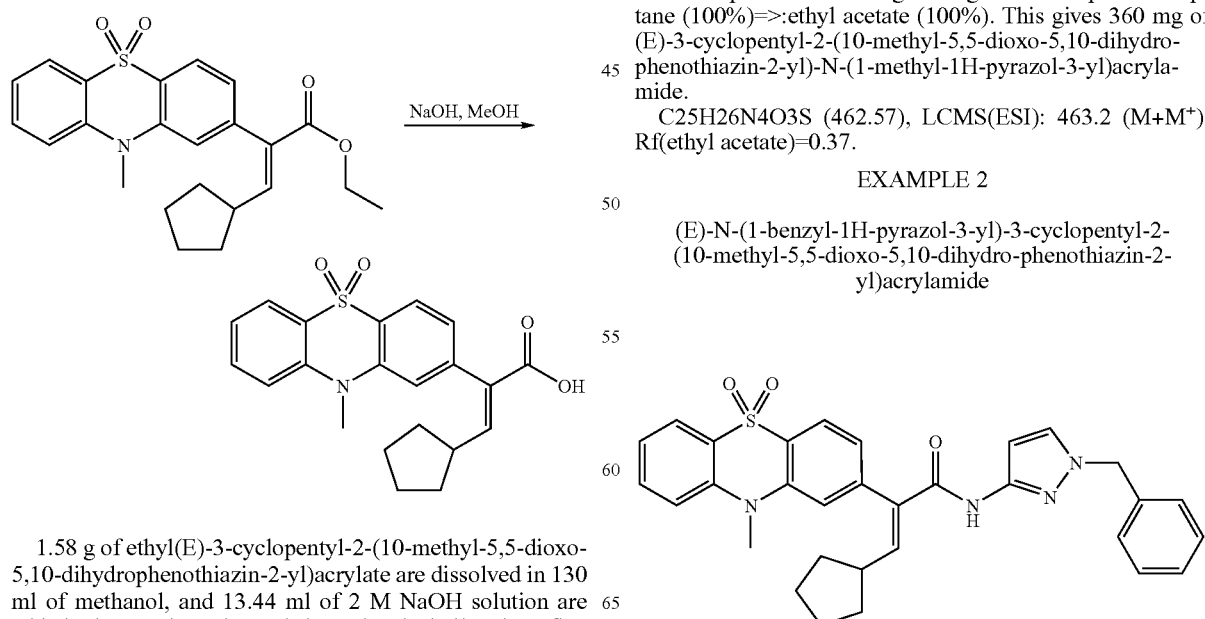

45

Analogously to example 1, (E)-3-cyclopentyl-2-(10-methyl-5,5-dioxo-5,10-dihydrophenothiazin-2-yl)acrylic acid and commercial 1-benzyl-1H-pyrazol-3-ylamine give (E)-N-(1-benzyl-1H-pyrazol-3-yl)-3-cyclopentyl-2-(10-methyl-5,5-dioxo-5,10-dihydrophenothiazin-2-yl)acrylamide.

C31H30N4O3S (538.67), LCMS(ESI): 539.3 (M+M$^+$), Rf(ethyl acetate)=0.69.

EXAMPLE 3

(E)-2-(5,5-dioxo-5,10-dihydrophenothiazin-2-yl)-N-(1-methyl-1H-pyrazol-3-yl)-3-(4-oxo-cyclohexyl)acrylamide

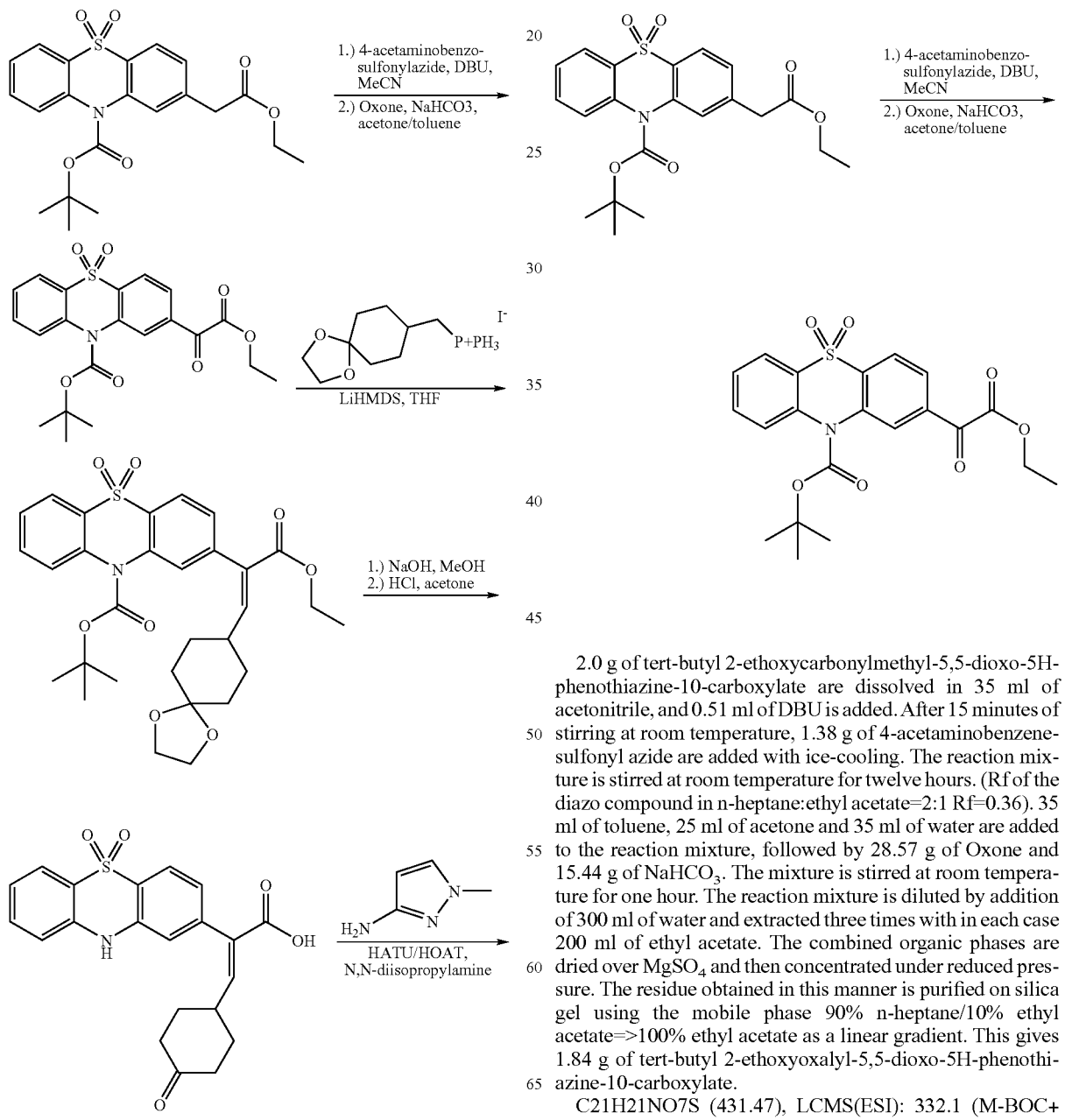

tert-butyl 2-ethoxyoxalyl-5,5-dioxo-5H-phenothiazine-10-carboxylate 2.0 g of tert-butyl 2-ethoxycarbonylmethyl-5,5-dioxo-5H-phenothiazine-10-carboxylate are dissolved in 35 ml of acetonitrile, and 0.51 ml of DBU is added. After 15 minutes of stirring at room temperature, 1.38 g of 4-acetaminobenzenesulfonyl azide are added with ice-cooling. The reaction mixture is stirred at room temperature for twelve hours. (Rf of the diazo compound in n-heptane:ethyl acetate=2:1 Rf=0.36). 35 ml of toluene, 25 ml of acetone and 35 ml of water are added to the reaction mixture, followed by 28.57 g of Oxone and 15.44 g of NaHCO$_3$. The mixture is stirred at room temperature for one hour. The reaction mixture is diluted by addition of 300 ml of water and extracted three times with in each case 200 ml of ethyl acetate. The combined organic phases are dried over MgSO$_4$ and then concentrated under reduced pressure. The residue obtained in this manner is purified on silica gel using the mobile phase 90% n-heptane/10% ethyl acetate=>100% ethyl acetate as a linear gradient. This gives 1.84 g of tert-butyl 2-ethoxyoxalyl-5,5-dioxo-5H-phenothiazine-10-carboxylate.

C21H21NO7S (431.47), LCMS(ESI): 332.1 (M-BOC+H$^+$), Rf(n-heptane:ethyl acetate=2:1)=0.29.

(1,4-dioxa-spiro[4.5]dec-8-ylmethyl)triphenylphosphoniumiodide

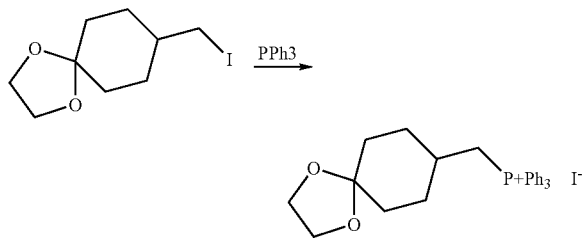

5.54 g of 8-iodomethyl-1,4-dioxa-spiro[4.5]decane and 5.15 g of triphenylphosphine are dissolved in 32 ml of acetonitrile and heated at the boil under reflux for 12 hours. The mixture is stirred at room temperature for two days and then concentrated under reduced pressure to a volume of about 15 ml, and 30 ml of diethyl ether are added. With vigorous stirring in an ice-bath, a precipitate begins to form. The precipitate is filtered off with suction and dried under reduced pressure. This gives 3.86 g of (1,4-dioxa-spiro[4.5]dec-8-ylmethyl)triphenylphosphoniumiodide.

C21H21NO7S (544.42, LCMS(ESI): 417.2 (M+).

tert-butyl 2-[(E)-2-(1,4-dioxa-spiro[4.5]dec-8-yl)-1-ethoxycarbonylvinyl]-5,5-dioxo-5H-phenothiazine-10-carboxylate

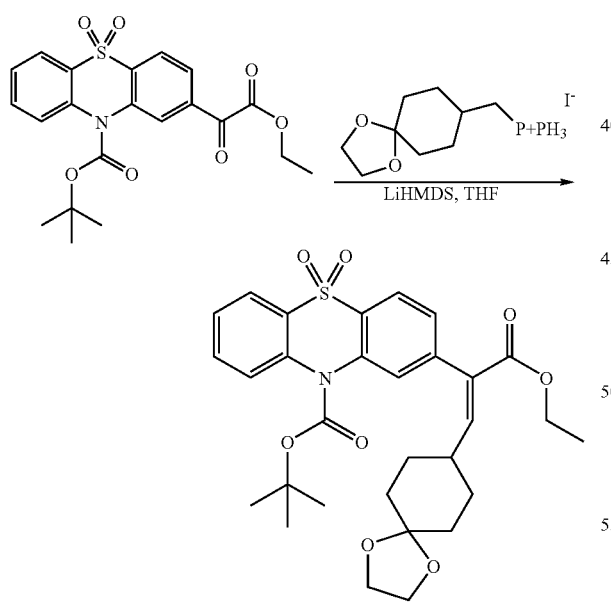

Under argon, 0.76 ml of 1,1,1,3,3,3-hexamethyldisilazane is dissolved in 20 ml of tetrahydrofuran. 1.32 ml of n-butyllithium (2.5 M in n-hexane) are added dropwise with ice-cooling, and the mixture stirred at 0° C. for 30 minutes.

This solution is then, with ice-cooling, added dropwise to a stirred suspension of 1.19 g of (1,4-dioxa-spiro[4.5]dec-8-ylmethyl)triphenylphosphonium iodide in 80 ml of tetrahydrofuran. The reaction mixture is stirred at 0° C. for 45 minutes, 1.80 g of tert-butyl 2-ethoxyoxalyl-5,5-dioxo-5H-phenothiazine-10-carboxylate, dissolved in 20 ml of THF, are then added dropwise, and the mixture stirred at 0° C. for one hour. The cooling bath is removed and the mixture is slowly warmed to room temperature. The reaction mixture is stirred at room temperature overnight. 30 ml of saturated sodium chloride solution are then added, and the mixture is extracted three times with in each case 100 ml of ethyl acetate. The combined organic phases are dried over MgSO4 and then concentrated under reduced pressure. The residue is purified on silica gel using the mobile phase 100% n-heptane=>ethyl acetate 100%. This gives 1.14 g of tert-butyl 2-[(E)-2-(1,4-dioxa-spiro[4.5]dec-8-yl)-1-ethoxycarbonylvinyl]-5,5-dioxo-5H-phenothiazine-10-carboxylate as light-yellow solid.

C30H35NO8S (569.68), LCMS(ESI): 587.2 (M+NH4+), 514.2 (M-tert-butyl+H+), 470.2 (M-BOC+H+), Rf(n-heptane:ethyl acetate=2:1)=0.16.

(E)-2-(5,5-dioxo-5,10-dihydrophenothiazin-2-yl)-3-(4-oxocyclohexyl)acrylic acid

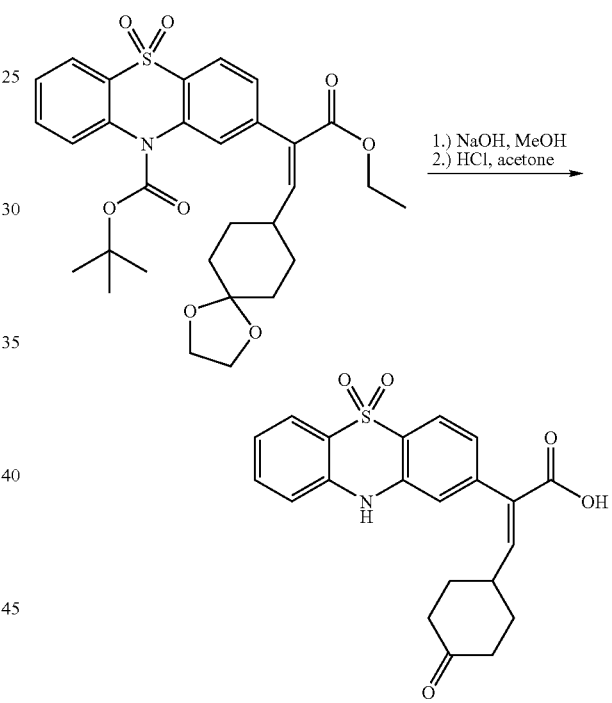

1.14 g of tert-butyl 2-[(E)-2-(1,4-dioxa-spiro[4.5]dec-8-yl)-1-ethoxycarbonylvinyl]-5,5-dioxo-5H-phenothiazine-10-carboxylate are dissolved in 130 ml of methanol, and 7.0 ml of a 2 M NaOH solution are added. The reaction mixture is heated at the boil under reflux for two hours. Methanol is removed under reduced pressure and the reaction mixture is adjusted to pH 4 by addition of concentrated hydrochloric acid. The precipitated solid is dissolved in 200 ml of ethyl acetate and dried over MgSO4, and the solvent is then removed under reduced pressure. The residue obtained in this manner is dissolved in 20 ml of acetone, and 4 ml of 50% strength hydrochloric acid solution are added. The reaction mixture is stirred at room temperature for 30 minutes. The acetone is removed under reduced pressure and the residue is taken up in 100 ml of water and 100 ml of ethyl acetate. The organic phase is dried over MgSO4, and the solvent is then removed under reduced pressure. This gives 840 mg of (E)-2-(5,5-dioxo-5,10-dihydrophenothiazin-2-yl)-3-(4-oxocyclohexyl)acrylic acid.

C21H19NO5S (397.45), LCMS(ESI): 398.2 (M+H+)

(E)-2-(5,5-dioxo-5,10-dihydrophenothiazin-2-yl)-N-(1-methyl-1H-pyrazol-3-yl)-3-(4-oxocyclohexyl)acrylamide

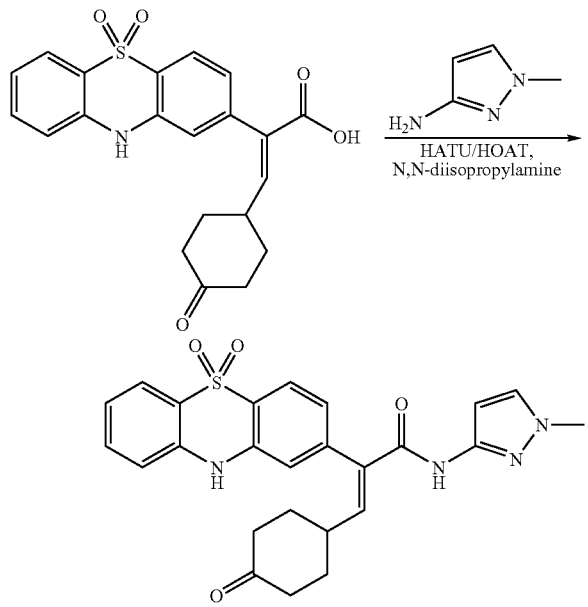

276 mg of (E)-2-(5,5-dioxo-5,10-dihydrophenothiazin-2-yl)-3-(4-oxocyclohexyl)acrylic acid, 101 mg of commercial 1-methyl-1H-pyrazol-3-ylamine and 0.61 ml of N,N-diisopropylethylamine are dissolved in 10 ml of dimethylformamide. 318 mg of HATU and 114 mg of HOAT are added, and the mixture stirred at room temperature for two hours. The reaction mixture is then diluted by addition of 100 ml of ethyl acetate and washed five times with in each case 30 ml of water. The organic phase is dried over MgSO$_4$, and the solvent is then removed under reduced pressure. The residue is purified on silica gel using the mobile phase n-heptane (100%)=>:ethyl acetate (100%). This gives 134 mg of (E)-2-(5,5-dioxo-5,10-dihydrophenothiazin-2-yl)-N-(1-methyl-1H-pyrazol-3-yl)-3-(4-oxocyclohexyl)acrylamide.

C25H24N4O4S (476.56), LCMS(ESI): 477.3 (M+H$^+$), 518.2 (M+MeCN+H$^+$), Rf(ethyl acetate)=0.10.

EXAMPLE 4

(E)-2-(5,5-dioxo-5,10-dihydrophenothiazin-2-yl)-N-(5-methoxythiazolo[5,4-b]pyridin-2-yl)-3-(4-oxocyclohexyl)acrylamide

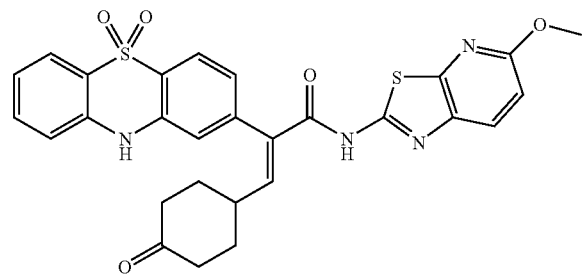

Analogously to example 3, (E)-2-(5,5-dioxo-5,10-dihydrophenothiazin-2-yl)-3-(4-oxocyclohexyl)acrylic acid and 5-methoxythiazolo[5,4-b]pyridin-2-ylamine give (E)-2-(5,5-dioxo-5,10-dihydrophenothiazin-2-yl)-N-(5-methoxythiazolo[5,4-b]pyridin-2-yl)-3-(4-oxocyclohexyl)acrylamide.

C28H24N4O5S2 (560.66), LCMS(ESI): 561.1 (M+M$^+$), Rf(ethyl acetate)=0.40.

EXAMPLE 5

(E)-N-(1-benzyl-1H-pyrazol-3-yl)-2-(5,5-dioxo-5,10-dihydrophenothiazin-2-yl)-3-(4-oxocyclohexyl)acrylamide

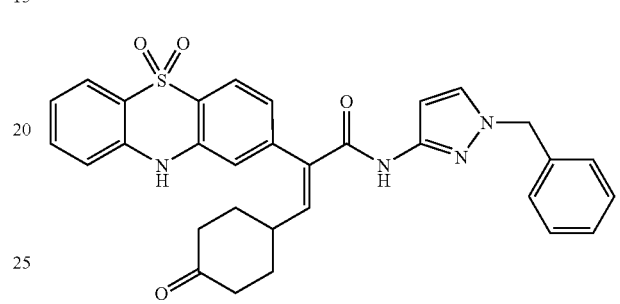

Analogously to example 3, (E)-2-(5,5-dioxo-5,10-dihydrophenothiazin-2-yl)-3-(4-oxocyclohexyl)acrylic acid and 1-benzyl-1H-pyrazol-3-ylamine give (E)-N-(1-benzyl-1H-pyrazol-3-yl)-2-(5,5-dioxo-5,10-dihydrophenothiazin-2-yl)-3-(4-oxocyclohexyl)acrylamide.

C31H28N4O4S (552.66), LCMS(ESI): 553.4 (M+H$^+$), Rf(ethyl acetate)=0.39.

We claim:
1. A compound of formula I

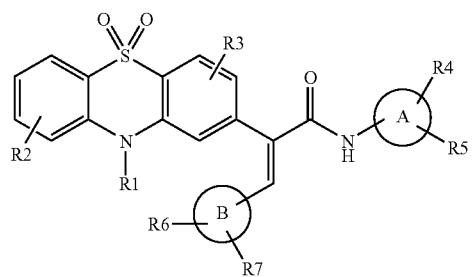

wherein:
R1 is H, $(C_1-C_6)$-alkyl, $(C_0-C_6)$-alkylene-aryl, CO—$(C_1-C_6)$-alkyl, $(C_2-C_6)$-alkylene-COO—$(C_0-C_6)$-alkyl, or $(C_2-C_6)$-alkylene-O—$(C_1-C_6)$-alkyl;
R2 and R3 are, independently, H, F, Cl, Br, CN, NO$_2$, $(C_0-C_6)$-alkylene-COO—$(C_0-C_6)$-alkyl, $(C_0-C_6)$-alkylene-O—$(C_0-C_6)$-alkyl, $(C_1-C_6)$-alkyl, $(C_0-C_6)$-alkylene-CO—$(C_1-C_6)$-alkyl, $(C_0-C_6)$-alkylene-phenyl, SCF$_3$, SF$_5$, or SCH$_3$;
R4 and R5 are, independently, H, F, Cl, Br, CN, SCN, NO$_2$, $(C_0-C_6)$-alkylene-COO—$(C_0-C_6)$-alkyl, —CO—COO—$(C_0-C_6)$-alkyl, $(C_0-C_6)$-alkylene-O—$(C_0-C_6)$-alkyl, $(C_1-C_6)$-alkyl, $(C_0-C_6)$-alkylene-CO—$(C_1-C_6)$-alkyl, $(C_0-C_6)$-alkylene-CONH($C_0-C_6$)-alkyl, $(C_0-C_6)$-alkylene-CON[$(C_0-C_6)$-alkyl]$_2$, $(C_0-C_6)$-alkylene-NH$(C_0-C_6)$-alkyl, $(C_0-C_6)$-alkylene-NH—COO—$(C_0-C_6)$- alkyl, $(C_0$-$C_6)$-alkylene-CON[$(C_0$-$C_6)$-alkyl]-O—$(C_0$-$C_6)$-alkyl, $(C_0$-$C_6)$-alkylene-N[$(C_0$-$C_6)$-alkyl]$_2$, $(C_0$-$C_6)$-alkylene-aryl, $SF_5$, $(C_0$-$C_6)$-alkyl-$S(O)_x(C_1$-$C_6)$-alkyl, $S(O)_x(C_1$-$C_6)$-alkylene-COO—$(C_0$-$C_6)$-alkyl, $S(O)_x(C_2$-$C_6)$-alkylene-O—$(C_0$-$C_6)$-alkyl, —$SO_2$—NH—$(C_0$-$C_6)$-alkyl, —$SO_2$—N—[$(C_0$-$C_6)$-alkyl]$_2$, $S(O)_x(C_0$-$C_6)$-alkylene-heterocycle, $S(O)_x(C_1$-$C_6)$-alkylene-CO-heterocycle, —NH—$SO_2$—$(C_1$-$C_6)$-alkyl, $(C_0$-$C_6)$-alkylene-cycloalkyl, $(C_0$-$C_6)$-alkylene-heterocycle, or $(C_0$-$C_6)$-alkylene-aryl;

R6 and R7 are, independently, H, F, Cl, Br, CN, $NO_2$, =O, =S, =N—O—$(C_0$-$C_6)$-alkyl, $(C_0$-$C_6)$-alkylene-COO—$(C_0$-$C_6)$-alkyl, $(C_0$-$C_6)$-alkylene-O—$(C_0$-$C_6)$-alkyl, $(C_0$-$C_6)$-alkylene-O—CO—$(C_1$-$C_6)$-alkyl, $(C_1$-$C_6)$-alkyl, $(C_0$-$C_6)$-alkylene-CO—$(C_1$-$C_6)$-alkyl,$(C_0$-$C_6)$-alkylene-aryl, $SF_5$, or $S(O)_x$—$(C_1$-$C_6)$-alkyl;

x is 0, 1 or 2;

A is a 5- to 10-membered heterocycle, wherein the heterocycle is optionally fused to a further 5- to 10-membered ring; and B is a 4- to 8-membered cycloalkyl ring, a 4- to 10-membered heterocycle or a 6- to 10-membered aryl ring;

or a physiologically acceptable salt thereof.

2. The compound according to claim 1, wherein
B is a 4- to 8-membered cycloalkyl ring;
or a physiologically acceptable salt thereof.

3. The compound according to claim 1, wherein
R2 and R3 are H;
R4 is $(C_1$-$C_6)$-alkyl, O—$(C_1$-$C_6)$-alkyl, or $(C_0$-$C_6)$-alkylene-aryl;
R5 is H; and
B is a 4- to 8-membered cycloalkyl ring;
or a physiologically acceptable salt thereof.

4. A pharmaceutical composition comprising the compound according to claim 1 or a physiologically tolerated salt thereof, in combination with a pharmacologically acceptable carrier or excipient.

5. A pharmaceutical composition comprising the compound according to claim 2 or a physiologically tolerated salt thereof, in combination with a pharmacologically acceptable carrier or excipient.

6. A pharmaceutical composition comprising the compound according to claim 3 or a physiologically tolerated salt thereof, in combination with a pharmacologically acceptable carrier or excipient.

7. The pharmaceutical composition according to claim 4, further comprising one additional active ingredient.

8. The pharmaceutical composition according to claim 7, wherein the additional active ingredient is selected from the group consisting of antidiabetics, hypoglycemic active ingredients, HMGCoA reductase inhibitors, cholesterol absorption inhibitors, PPAR gamma agonists, PPAR alpha agonists, PPAR alpha/gamma agonists, PPAR delta agonists, fibrates, MTP inhibitors, bile acid absorption inhibitors, CETP inhibitors, polymeric bile acid adsorbents, LDL receptor inducers, ACAT inhibitors, antioxidants, lipoprotein lipase inhibitors, ATP-citrate lyase inhibitors, squalene synthetase inhibitors, lipoprotein(a) antagonists, HM74A receptor agonists, lipase inhibitors, insulins, sulfonylureas, biguanides, meglitinides, thiazolidinediones, α-glucosidase inhibitors, active ingredients which act on the ATP-dependent potassium channel of the beta cells, glycogen phosphorylase inhibitors, glucagon receptor antagonists, activators of glucokinase, inhibitors of gluconeogenesis, inhibitors of fructose-1,6-biphosphatase, modulators of glucose transporter 4, inhibitors of glutamine-fructose-6-phosphate amidotransferase, inhibitors of dipeptidylpeptidase IV, inhibitors of 11-beta-hydroxysteroid dehydrogenase 1, inhibitors of protein tyrosine phosphatase 1B, modulators of the sodium-dependent glucose transporter 1 or 2, GPR40 modulators, inhibitors of hormone-sensitive lipase, inhibitors of acetyl-CoA carboxylase, inhibitors of phosphoenolpyruvate carboxykinase, inhibitors of glycogen synthase kinase-3 beta, inhibitors of protein kinase C beta, endothelin-A receptor antagonists, inhibitors of I kappaB kinase, modulators of the glucocorticoid receptor, CART agonists, NPY agonists, MC4 agonists, orexin agonists, H3 agonists, TNF agonists, CRF agonists, CRF BP antagonists, urocortin agonists, β3 agonists, CB1 receptor antagonists, melanocyte-stimulating hormone agonists, CCK agonists, serotonin reuptake inhibitors, mixed serotoninergic and noradrenergic compounds, 5HT agonists, bombesin agonists, galanin antagonists, human growth hormones, growth hormone-releasing compounds, diphenylazetidinone derivative, TRH agonists, uncoupling protein 2 or 3 modulators, leptin agonists, DA agonists (bromocriptine, Doprexin), lipase/amylase inhibitors, PPAR modulators, RXR modulators, TR-β agonists and amphetamines.

9. A process for producing a pharmaceutical composition comprising the compound according to claim 1 or a physiologically tolerated salt thereof, in combination with a pharmacologically acceptable carrier or excipient, comprising mixing the compound according to claim 1 or the physiologically tolerated salt thereof with the pharmacologically acceptable carrier or excipient, and converting this mixture into a form suitable for administration.

\* \* \* \* \*